United States Patent
Kester et al.

(10) Patent No.: US 10,272,041 B2
(45) Date of Patent: Apr. 30, 2019

(54) ACID STABLE LIPOSOMAL COMPOSITIONS AND METHODS FOR PRODUCING THE SAME

(71) Applicant: The Penn State Research Foundation, University Park, PA (US)

(72) Inventors: Mark Kester, Harrisburg, PA (US); Karam El-Bayoumy, Hummelstown, PA (US); Christine Skibinski, Hershey, PA (US); Arunangshu Das, Hummelstown, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 106 days.

(21) Appl. No.: 14/211,957

(22) Filed: Mar. 14, 2014

(65) Prior Publication Data

US 2014/0271824 A1 Sep. 18, 2014

Related U.S. Application Data

(60) Provisional application No. 61/788,564, filed on Mar. 15, 2013, provisional application No. 61/897,642, filed on Oct. 30, 2013.

(51) Int. Cl.
*A61K 9/127* (2006.01)
*A61K 38/28* (2006.01)
*A61K 31/202* (2006.01)

(52) U.S. Cl.
CPC ............ *A61K 9/127* (2013.01); *A61K 9/1271* (2013.01); *A61K 31/202* (2013.01); *A61K 38/28* (2013.01); *A61K 9/1278* (2013.01)

(58) Field of Classification Search
None
See application file for complete search history.

(56) References Cited

U.S. PATENT DOCUMENTS

| | | | |
|---|---|---|---|
| 2003/0147944 A1* | 8/2003 | Mayer et al. | 424/450 |
| 2004/0247660 A1* | 12/2004 | Singh | A61K 9/0019 424/450 |
| 2008/0220028 A1* | 9/2008 | Patel et al. | 424/400 |
| 2011/0064794 A1* | 3/2011 | Deng et al. | 424/450 |

FOREIGN PATENT DOCUMENTS

| | | | |
|---|---|---|---|
| WO | WO 99/10337 | | 3/1999 |
| WO | WO-2012088414 | * | 6/2012 |

OTHER PUBLICATIONS

Benvegnu T, Archaeosomes based on novel synthetic tetraethery-type lipids for the development of oral delivery systems, Chem Commun, 2005, 5536-5538.*
Patel, Intl J Pharm, 2000, 194, 39-49.*
Sprott et al (FEMS Microbiology Letters, 154, 1997, 17-22).*
Eckert et al., "Liposome-incorporated DHA increases neuronal survival by enhancing non-amyloidogenic APP processing," *Biochimica et Biophysica Acta*, 2011, 1808:236-243.
Hossain et al., "Docosahexaenoic acid and eicosapentaenoic acid-enriched phosphatidylcholine liposomes enhance the permeability, transportation and uptake of phospholipids in Caco-2 cells," *Molecular and Cellular Biochemistry*, 2006, 285:155-163.
Ichihara et al., "Therapeutic Effects of Hybrid Liposomes Composed of Phosphatidylcholine and Docosahexaenoic Acid on the Hepatic Metastasis of Colon Carcinoma along with Apoptosis in Vivo," *Biol. Pharm. Bull.*, 2011, 34(6):901-905.
Patel et al., 2000, "In vitro assessment of archaeosome stability for developing oral delivery systems" Int J Pharm 194 (1):39-49.
Khosravi-Darani et al., 2010, "Nanoliposome potentials in nanotherapy: A concise overview" Int J Nanosci Nantechnol 6(1):3-13.
Kohli et al., 2006, "Tethered Lipid bilayers on electrolessly deposit gold for bioelectronics applications" Biomacromolecules 7(12):3327-3335.

* cited by examiner

*Primary Examiner* — Brian Gulledge
(74) *Attorney, Agent, or Firm* — Riverside Law LLP

(57) ABSTRACT

The present invention relates to a liposomal formulation for oral delivery of a bioactive agent that considers pH stability and oxidative stability of a bioactive ingredient. These lipid formulations are superior to conventional liposomes due to their stability, thereby circumventing the need for intravenous delivery of bioactive agents. In one embodiment, the methods and compositions of the present invention relate to the oral delivery of insulin or a prodrug thereof.

12 Claims, 18 Drawing Sheets

Day 63 stability testing of ORAL Liposomes

GHOST

Insulin-ORAL pH7 pH1

ACID STABLE LIPOSOMAL COMPOSITIONS AND METHODS FOR PRODUCING THE SAME

CROSS-REFERENCE TO RELATED APPLICATIONS

The present application claims priority to U.S. Provisional Patent Application No. 61/788,564 filed Mar. 15, 2013, and U.S. Provisional Patent Application No. 61/897,642 filed Oct. 30, 2013, both of which are incorporated by reference herein in their entirety.

FIELD OF THE INVENTION

Embodiments of the invention relate to lipid formulations which are stable for oral administration of a bioactive agent. Methods of producing the formulations for encapsulation of bioactive agents and treatment of diseases or disorders are provided.

BACKGROUND

Liposomes are microscopic particles that are made up of one or more lipid bilayers enclosing an internal compartment. Liposomes can be categorized into multilamellar vesicles, multivesicular liposomes, unilamellar vesicles and giant liposomes. Liposomes have been widely used as carriers for a variety of agents such as drugs, cosmetics, diagnostic reagents, and genetic material. Since liposomes consist of non-toxic lipids, they generally have low toxicity and therefore are useful in a variety of pharmaceutical applications. In particular, liposomes are useful for increasing the circulation lifetime of agents that have a short half-life in the bloodstream. Liposome encapsulated drugs often have biodistributions and toxicities which differ greatly from those of free drug. For specific in vivo delivery, the sizes, charges and surface properties of these carriers can be changed by varying the preparation methods and by tailoring the lipid makeup of the carrier. For instance, liposomes may be made to release a drug more quickly by decreasing the acyl chain length of a lipid making up the carrier. However, conventional liposomes are not stable enough for oral administration of a bioactive agent, as the liposomes cannot withstand the harsh in vivo environments and degrade resulting in the bioactive agent being destroyed.

Thus, there is a need in the art for liposomes having the required stability for the oral delivery of a bioactive agent. The present invention addresses this unmet need in the art.

SUMMARY OF THE INVENTION

The present invention relates to oral liposomal compositions or formulations that exhibit oxidative and pH stability when administered by oral delivery, and methods for producing such compositions. These formulations allow for an increase in bioavailability of a bioactive agent, such as for example, stability of DHA in circulation and at the breast tissue leading to the prevention of breast cancer.

In one embodiment, the composition of the present invention comprises one or more lipid molecules encapsulating one or more bioactive agents, wherein the lipid molecules comprise a polyol backbone formulated for oral administration and delivery of the bioactive agent(s). In one embodiment, the lipid molecules comprise one or more groups linked to the polyol backbone via ether linkages. In another embodiment, the polyol backbone comprises an archaeal core lipid. In some embodiments, the archaeal core lipid can be archaeol (2,3-di-O-diphytanyl-sn-glycerol) or caldarchaeol (2,2',3,3'-tetra-O-dibiphytanyl-sn-diglycerol). In various embodiments, the lipid molecules can further comprise one or more branched alkyl groups, alkene groups, alkenyl groups or combinations thereof. The lipid molecules can comprise one or more saturated alkyl chains with methyl branching attached to glycerol by linkages comprising ether linkages, methyl carbamyl linkages, or combinations thereof. In various embodiments, the lipid molecule formulation for encapsulating a bioactive agent can comprise a liposome, a nanoliposome, a niosome, a microsphere, a nanosphere, a nanoparticle, a micelle, an exosome or an archaeosome. In one embodiment, the lipid molecule formulation is stable in pH levels of at least about pH.

The present invention also relates to methods for producing the liposomal compositions or formulations. In one embodiment, the method of the present invention is a method of producing a carrier complex comprising the steps of: drying a lipid solution having one or more archaeo-type lipid molecules under a nitrogen atmosphere wherein the lipid solution further comprises at least one bioactive agent in a therapeutically effective amount; rehydrating the lipid solution; heating the solution to at least about 50° C.; sonicating the rehydrated lipid solution; performing a sizing step, and removing excess bioactive agent. In one embodiment, the carrier complex comprises uniformly sized particles wherein the particles comprise: liposomes, nanoliposomes, niosomes, microspheres, nanospheres, nanoparticles, micelles or archaeosomes. In one embodiment, the carrier complex is a nanoliposome having a diameter of between about 20 to 200 nm. In one embodiment, the lipid molecules comprise one or more ether linkages. In one embodiment, the lipid molecules further comprise one or more branched methyl groups. In one embodiment, the lipid molecules comprise one or more saturated alkyl chains with methyl branching attached to glycerol by ether linkages.

In various embodiments, the compositions and methods relate to delivery of a bioactive agent. The bioactive agent can comprise, for example, fatty acids, hormones, enzymes, isotopes, dyes, metals, chemotherapeutic agents, immunotherapeutic agents, proteins, peptides, nucleic acids, synthetic or natural compounds. In one embodiment, the bioactive agent is an omega-3 fatty acid. In another embodiment, the bioactive agent is insulin or pro-drug thereof. In yet another embodiment, the bioactive agent is a fatty-acyl insulin derivative.

In various embodiments, the method of the present invention relates to a method for treating a disease using the compositions described herein. In one embodiment, the method is a method of treating cancer comprising administering to a patient in need thereof, a nanoliposome containing one or more bioactive agents in a therapeutically effective amount. In one embodiment, the nanoliposome is administered orally. In one embodiment, the bioactive agent is an omega-3 fatty acid.

In various embodiments, the present invention relates to liposomal formulations. In one embodiment, the liposomal formulation comprises 1,2-di-O-hexadecyl-sn-glycero-3-phosphatidylcholine and 1,2-di-O-phytanyl-sn-glycero-3-phosphatidylethanolamine. In one embodiment, the 1,2-di-O-hexadecyl-sn-glycero-3-phosphatidylcholine and 1,2-di-O-phytanyl-sn-glycero-3-phosphatidylethanolamine form uniformly sized particles wherein the particles comprise: liposomes, nanoliposomes, niosomes, microspheres, nanospheres, nanoparticles, micelles or archaeosomes. In one embodiment, the uniformly sized particles encapsulate a bioactive agent. In one embodiment, the bioactive agent is insulin or a pro-drug thereof. In one embodiment, the particles are formulated to have a molar ratio of: 1,2-di-O-hexadecyl-sn-glycero-3-phosphatidylcholine, 1,2-di-O-phytanyl-sn-glycero-3-phosphatidylethanolamine and bioactive agent of 6:3:1. In one embodiment, the bioactive agent is docosahexanoic acid (DHA).

In one embodiment, the particles of the liposomal formulation further comprise a PEGylated lipid. In one embodiment, the particles comprise up to 20 molar percent of the PEGylated lipid. In one embodiment, the PEGylated lipid is 1,2-di-O-phytanyl-sn-glycero-3-phosphatidylethanolamine-PEG2000. In another embodiment, the PEGylated lipid is 1,2 distearoyl-phosphatidylethanolamine-PEG2000. In one embodiment, the formulation has a molar ratio of 1,2-di-O-hexadecyl-sn-glycero-3-phosphatidylcholine: 1,2-di-O-phytanyl-sn-glycero-3-phosphatidylethanolamine: PEGylated lipid of 5:3:2. In one embodiment, the formulation has a molar ratio of 1,2-di-O-hexadecyl-sn-glycero-3-phosphatidylcholine: 1,2-di-O-phytanyl-sn-glycero-3-phosphatidylethanolamine: PEGylated lipid of 4.5:4.0:1.5. In one embodiment, the formulation has a molar ratio of 1,2-di-O-hexadecyl-sn-glycero-3-phosphatidylcholine: 1,2-di-O-phytanyl-sn-glycero-3-phosphatidylethanolamine: 1,2-di-O-phytanyl-sn-glycero-3-phosphatidylethanolamine-PEG2000 of 5:3:2. In one embodiment, the formulation has a molar ratio of: 1,2-di-O-hexadecyl-sn-glycero-3-phosphatidylcholine: 1,2-di-O-phytanyl-sn-glycero-3-phosphatidylethanolamine: 1,2 distearoyl-phosphatidylethanolamine-PEG2000 of 4.5:4.0:1.5. In one embodiment, the formulation has a molar ratio of: 1,2-di-O-hexadecyl-sn-glycero-3-phosphatidylcholine: 1,2-di-O-phytanyl-sn-glycero-3-phosphatidylethanolamine: 1,2-di-O-phytanyl-sn-glycero-3-phosphatidylethanolamine-PEG2000 of 4.5:4.0:1.5. In one embodiment, the liposomal formulation has a molar ratio of phosphatidylcholine: phosphatidylethanolamine of about 2:1 to 2:3. In one embodiment, the liposomal formulation has a molar ratio of phosphatidylcholine: phosphatidylethanolamine of about 9:11.

In another embodiment, the present invention relates to a composition for encapsulating a biological agent, comprising at least one lipid, wherein the at least one lipid comprises a polyol backbone formulated for oral administration and delivery of the bioactive agent. In one embodiment, the biological agent is insulin or a prodrug thereof. In one embodiment, the at least one lipid is selected from the group comprising 1,2-di-O-hexadecyl-sn-glycero-3-phosphatidylcholine, 1,2-di-O-phytanyl-sn-glycero-3-phosphatidylethanolamine, and 1,2 distearoyl-phosphatidylethanolamine. In another embodiment, the at least one lipid is PEGylated. In another embodiment, the at least one lipid comprises a mixture having a molar ratio of 5:3:2 1,2-di-O-hexadecyl-sn-glycero-3-phosphatidylcholine: 1,2-di-O-phytanyl-sn-glycero-3-phosphatidylethanolamine: 1,2-di-O-phytanyl-sn-glycero-3-phosphatidylethanolamine-PEG2000.

BRIEF DESCRIPTION OF THE DRAWINGS

FIGS. 11A through 11D, is a set of graphs showing size distribution by intensity for ORAL liposomes and conventional liposomes. ORAL liposomes (i.e., exemplary liposomes of the present invention) or conventional liposomes (4 batches each) were incubated for two hours at 37° C. at pH=1 and their size/distribution were measured using Dynamic Light Scattering. FIGS. 11A (size/distribution at 10 min.) and 11B (size/distribution at 2 h) show that the ORAL liposomes maintained integrity as demonstrated by the single peak. The multiple peaks in FIG. 11C (size/distribution at 10 min.) and 11D (size/distribution at 2 h) indicate the conventional liposomes are agglomerating.

FIG. 12, comprising FIG. 12D is a graph showing % channel vs. size for insulin-ORAL at pH, 7 (unadjusted), 3, and 1, wherein the data shown was measured 30 min after pH adjustment.

DETAILED DESCRIPTION

Figure 1:
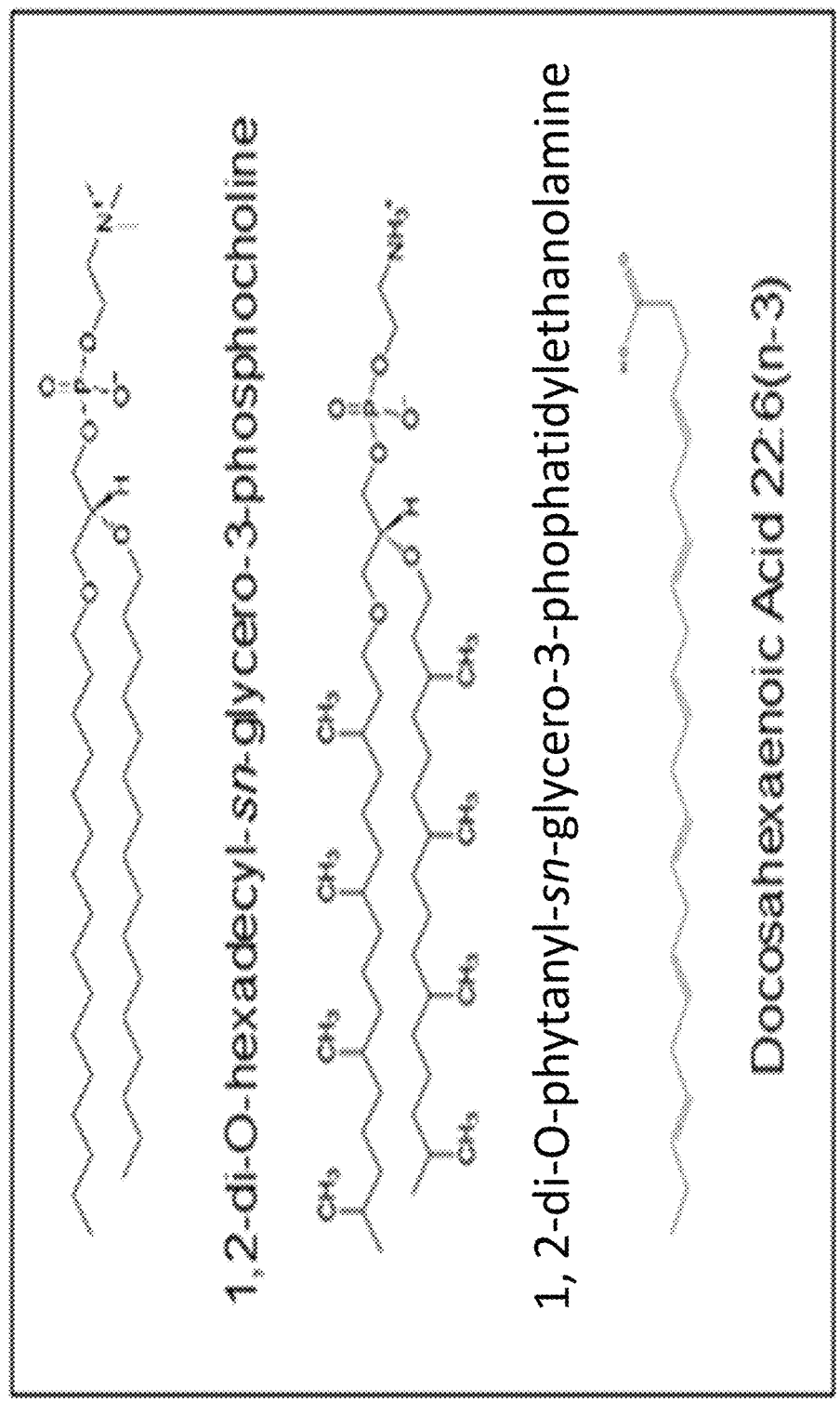
FIG. 1 is a schematic representation of the structure of the components for Docosahexanoic acid (DHA) ether lipid based liposome.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Definitions

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "archaeal lipid" refers to a polar lipid common to the Domain Archaea typified by isoprenoid chains in ether linkage to the sn-2,3 carbons of the glycerol backbone. Archaeal core lipids are most commonly 2,3-di-O-sn-diphytanylglycerol (archaeol), and 2,2',3,3'-tetra-O-dibiphytanyl-sn-diglycerol (caldarchaeol). Synthetic archaeal lipids or polar synthetic lipids refer to core lipid precursors either derived from Archaeal lipids by hydrolysis or made by chemical synthesis, conjugated to at least one new head group. Archaeol phospholipids are referred to using archaetidyl, for example, AG, archaetidylglycerol; AS, archaetidylserine.

The term "conventional lipids" refers to the lipids common to the Domains Bacteria and Eukarya. This includes polar lipids typified by fatty acyl chains in ester linkage to the sn-1,2 carbons of the glycerol backbone, and neutral lipids such as cholesterol. Conventional phospholipids are referred to in the usual way, for example, DPPG, dipalmitoylphosphatidylglycerol; DPPS, dipalmitoylphosphatidylserine.

"Archaeosomes" refer to closed lipid vesicles that contain any amount of synthetic archaeal lipid(s).

The term "stable," when applied to the compositions herein, means that the compositions maintain one or more aspects of their physical structure (e.g., size range and/or distribution of particles) over a period of time. In some embodiments, a stable liposome or nanoparticle composition is one for which the average particle size, the maximum particle size, the range of particle sizes, and/or the distribution of particle sizes (i.e., the percentage of particles above a designated size and/or outside a designated range of sizes) is maintained for a period of time and over a range of pH and temperatures. In some embodiments, a stable composition is one for which a biologically relevant activity is maintained for a period of time. In some embodiments, the period of time is at least about one hour; in some embodiments the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. For example, if a population of liposomes or nanoparticles comprising the embodied lipid formulations is subjected to prolonged storage, temperature changes, and/or pH changes, and a majority of the nanoparticles in the composition maintain a diameter within a stated range (for example, between approximately 10 nm and approximately 120 nm), the nanoparticle composition is stable. For some such populations, a majority is more than about 50%, about 60%, about 70%, about 80%, about 90%, about 95%, about 96%, about 97%, about 98%, about 99%, about 99.5%, about 99.6%, about 99.7%, about 99.8%, about 99.9% or more.

As used herein, the term "oligonucleotide specific for" refers to an oligonucleotide having a sequence (i) capable of forming a stable complex with a portion of the targeted gene, or (ii) capable of forming a stable duplex with a portion of a mRNA transcript of the targeted gene.

As used herein, the term "oligonucleotide," is meant to encompass all forms or desired RNA, RNA/DNA molecules which modulate gene expression and/or function, and includes without limitation: "siRNA," "shRNA" "antisense oligonucleotide" etc. The term also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoögsteen or reverse Hoogsteen types of base pairing, or the like.

The oligonucleotides may be "chimeric," that is, composed of different regions. In some embodiments of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotide compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register," that is, when the monomers are linked consecutively, as in native DNA, or linked via spacers. The spacers are intended to constitute a covalent "bridge" between the regions and have in preferred cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

"Analogs" in reference to nucleosides includes synthetic nucleosides having modified base moieties and/or modified sugar moieties, e.g., described generally by Scheit, Nucleotide Analogs, John Wiley, New York, 1980; Freier & Altmann, *Nucl. Acid. Res.*, 1997, 25(22), 4429-4443, Toulmé, J. J., *Nature* Biotechnology 19:17-18 (2001); Manoharan M., *Biochemica et Biophysica Acta* 1489:117-139 (1999); Freier S., M., *Nucleic Acid Research*, 25:4429-4443 (1997), Uhlman, E., *Drug Discovery & Development*, 3: 203-213 (2000), Herdewin P., *Antisense & Nucleic Acid Drug Dev.*, 10:297-310 (2000),); 2'-O, 3'-C-linked [3.2.0]bicycloarabinonucleosides (see e.g. N. K Christiensen., et al, *J. Am. Chem. Soc.*, 120: 5458-5463 (1998). Such analogs include synthetic nucleosides designed to enhance binding properties, e.g., duplex or triplex stability, specificity, or the like.

As used herein, the term "gene" means the gene and all currently known variants thereof and any further variants which may be elucidated.

As used herein, "variant" of polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological activity may be found using computer programs well known in the art, for example, LASERGENE software (DNASTAR).

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type target gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

As used herein, the term "mRNA" means the presently known mRNA transcript(s) of a targeted gene, and any further transcripts which may be elucidated.

By "desired RNA" molecule is meant any foreign RNA molecule which is useful from a therapeutic, diagnostic, or other viewpoint. Such molecules include antisense RNA molecules, decoy RNA molecules, enzymatic RNA, therapeutic editing RNA and agonist and antagonist RNA.

By "antisense RNA" is meant a non-enzymatic RNA molecule that binds to another RNA (target RNA) by means of RNA-RNA interactions and alters the activity of the target RNA (Eguchi et al., 1991 *Annu. Rev. Biochem.* 60, 631-652).

RNA interference "RNAi" is mediated by double stranded RNA (dsRNA) molecules that have sequence-specific homology to their "target" nucleic acid sequences (Caplen, N. J., et al., *Proc. Natl. Acad. Sci. USA* 98:9742-9747 (2001)). In certain embodiments of the present invention, the mediators of RNA-dependent gene silencing are oligonucleotide nucleotide "small interfering" RNA duplexes (siRNAs). The siRNAs are derived from the processing of dsRNA by an RNase enzyme known as Dicer (Bernstein, E., et al., *Nature* 409:363-366 (2001)). siRNA duplex products are recruited into a multi-protein siRNA complex termed RISC(RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion (Bernstein, E., et al., *Nature* 409:363-366 (2001); Boutla, A., et al., *Curr. Biol.* 11:1776-1780 (2001)). Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 0 to about 50 nucleotides (nt). In examples of non-limiting embodiments, oligonucleotides can comprise about 5 to about 40 nt, about 5 to about 30 nt, about 10 to about 30 nt, about 15 to about 25 nt, or about 20-25 nucleotides.

As used herein, the term "alkenyl" as a group or a part of a group refers to an optionally substituted straight or branched hydrocarbon chain containing the specified number of carbon atoms and containing at least one double bond.

For example, the term "$C_{2-6}$ alkenyl" means a straight or branched alkenyl containing at least 2 and at most 10 carbon atoms and containing at least one double bond. Multiple double bonds may be adjacent (=C=), conjugated (=C—C=), or are non-adjacent and non-conjugated. In particular, multiple double bonds are conjugated, or are non-adjacent and non-conjugated. It will be appreciated that in groups of the form —O—$C_{2-6}$ alkenyl, the double bond is preferably not adjacent to the oxygen. Preferably, the alkenyl groups of the invention may be optionally substituted and have at least 2 carbon atoms (and all combinations and subcombinations of ranges and specific numbers of carbon atoms therein). Examples of "alkenyl" as used herein include, but are not limited to, ethenyl, 2-propenyl, 3-butenyl, 2-butenyl, 2-pentenyl, 3-pentenyl, 3-methyl-2-butenyl, 3-methylbut-2-enyl, 3-hexenyl and 1,1-dimethylbut-2-enyl.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

"Treatment" is an intervention performed with the intention of preventing the development or altering the pathology or symptoms of a disorder. Accordingly, "treatment" refers to both therapeutic treatment and prophylactic or preventative measures. "Treatment" may also be specified as palliative care. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. Accordingly, "treating" or "treatment" of a state, disorder or condition includes: (1) preventing or delaying the appearance of clinical symptoms of the state, disorder or condition developing in a human or other mammal that may be afflicted with or predisposed to the state, disorder or condition but does not yet experience or display clinical or subclinical symptoms of the state, disorder or condition; (2) inhibiting the state, disorder or condition, i.e., arresting, reducing or delaying the development of the disease or a relapse thereof (in case of maintenance treatment) or at least one clinical or subclinical symptom thereof; or (3) relieving the disease, i.e., causing regression of the state, disorder or condition or at least one of its clinical or subclinical symptoms. The benefit to an individual to be treated is either statistically significant or at least perceptible to the patient or to the physician.

The term "insulin", as used herein, refers to any naturally occurring or recombinant insulin, for example, insulin analogs and derivatives. Insulin from any suitable species can be used, such as human, pig, cow, dog, sheep. In a preferred embodiment, the insulin is porcine insulin. "Regular insulin" as disclosed herein may refer to naturally-occurring insulin or synthetic insulin molecule. Naturally-occurring insulin or synthetic insulin molecule may include, but not limited to, monomeric, polymeric and/or fibril-like insulin, and different forms of insulin molecule depends on different pH values.

Lipid Formulations

Lipids that can endure an environment of high acidity and temperature are ideal for an orally administered liposome and have been discovered in archaeobacteria. This organism is composed of unique membrane lipids that contain saturated alkyl chains with methyl branching attached to glycerol by ether linkages. The ether linkages of these lipids are stable over a variety of temperatures and are more resistant to attack by phospholipases than ester-based lipids. The branched methyl groups provide a means of reducing membrane permeability and increase stability at low pH levels.

In embodiments, a liposomal formulation comprises one or more lipid molecules having stable ether linkages. In preferred embodiments, a liposome comprises lipids similar in structure to lipids found in archaeobacteria. In embodiments, the liposomes comprise lipid formulations of glycerol-ether lipids. Ether bonds are chemically more resistant than ester bonds and this stability results in liposomes which are resistant to enzymatic cleavage, degradation, high temperatures and very acidic or alkaline conditions as compared to liposomes. In other embodiments, the lipids comprise Archeal lipid tail motifs.

Archaeal lipids are based upon the isoprenoid sidechain and are long chains with multiple side-branches and sometimes even cyclopropane or cyclohexane rings. This is in contrast to the fatty acids found in other organisms' membranes, which have straight chains with no branches or rings. In some archaea the lipid bilayer is replaced by a monolayer. In effect, the archaea fuse the tails of two independent phospholipid molecules into a single molecule with two polar heads (a bolaamphiphile); this fusion may make their membranes more rigid and better able to resist harsh environments. For example, the lipids in Ferroplasma are of this type, which is thought to aid this organism's survival in its highly acidic habitat.

In preferred embodiments, the liposomes comprising one or more lipid formulations is resistant to pH levels commonly found in the stomach and/or intestines of an animal, for example, a human. In another embodiment, the liposomes comprise one or more lipid formulations resistant to enzymes, acids or other compounds commonly found in the stomach and digestive track of an animal. These formulations can be manipulated to vary with the type of conditions encountered in vivo after oral delivery, for example, the liposomes may be formulated to dissolve slowly under pH conditions in the stomach and/or resistance to digestive enzymes. The formulations of the liposomes can thus be manipulated based on a desired purpose. In one embodiment, a liposome comprises one or more ether lipids. For example, 1,2-di-O-hexadecyl-sn-glycero-3-phosphatidylcholine, 1,2-di-O-phytanyl-sn-glycero-3-phosphatidylethanolamine, and/or 1,2-di-O-phytanyl-sn-glycero-3-phosphatidylcholine which are similar in structure to archaeol-based ether lipids. These lipids contain ether bonds and methyl branching, both characteristics of archaeol lipids. A liposome comprising these lipids would be less susceptible to phospholipase hydrolysis and changes in pH. Thus these liposomes are effective in oral delivery of bioactive agents without the need for intra-venous infusion. The advantages of oral delivery of bioactive agents that prior to this invention are many, including long term storage of these bioactive agents. In preferred embodiments, a bioactive agent is insulin. Oral delivery of insulin would be preferable to the current methodology for storing and delivery of insulin to patients.

In some embodiments, the nanoliposome has a diameter of between about 20-200 nm, preferably between about 70-90 nm.

In some embodiments, a composition comprises one or more lipid molecules encapsulating one or more bioactive agents, wherein the lipid molecules comprise an archaeal core lipid, and are formulated for oral administration and delivery of the bioactive agent(s). In embodiments, the lipid molecules comprise a polyol backbone, such as for example, glycerol.

In some embodiments, the lipid molecules comprise one or more groups linked to the polyol backbone via ether linkages.

In other embodiments, an archaeal core lipid comprises archaeol (2,3-di-O-diphytanyl-sn-glycerol) or caldarchaeol (2,2',3,3'-tetra-O-dibiphytanyl-sn-diglycerol).

In some embodiments, the lipid molecules further comprise one or more branched alkyl groups. In preferred embodiments, the lipid molecules comprise one or more saturated alkyl chains with methyl branching attached to glycerol by ether linkages.

Bioactive Agents.

Recent preclinical data has shown that omega-3 fatty acids have a chemopreventive effect in breast cancer, especially when given in a high amount (Zhu Z., et al., *Cancer Preventive Research* 2011; 4:1675-1685). In high amounts, omega-3 fatty acids have shown to influence cell signaling pathways that include cell proliferation and death, inflammation, and lipid synthesis (Weiqin J. et al., *Cancer Research;* 72(15) 3795-806, 2012).

Docosahexanoic acid (DHA, 22:6 n-3), a component in fish oil, has been evaluated in preclinical models and has shown to be the most effective of the omega-3s in the prevention of breast cancer (Noguchi M. et al., British Journal of Cancer (1997) 75(3), 348-353; Yuri T., et al. *Nutrition and Cancer,* 45(2), 2003, 211-217; Manni A., et al., *Cancer Preventive Research,* 2010 March; 3(3):322-30). However, bioavailability of DHA is very low since mammals cannot synthesize the acid and the Western Diet, with a ratio of 15:1 omega-6:omega-3 fatty acids, is not sufficient in providing the levels of DHA required for cancer prevention. A liposomal formulation for DHA for intravenous administration has been developed (Hossain Z. et al. *Molecular and Cellular Biochemistry* 285:155-163. 2006; Eckert G. P. et al. *Biochimica et Biophysica Acta,* 1808 (2011) 236-243; Ichihara H. *Biol. Pharm. Bull.* 34(6) 901-905 (2014), however, a formulation for oral delivery that considers pH stability and oxidative stability of DHA would be superior for chemoprevention.

In another embodiment, a carrier complex or liposomal formulation encapsulates a bioactive agent wherein the liposomal formulation is stable for oral administration of the bioactive agent. In preferred embodiments, the encapsulation efficiency is at least about 70%. More preferably, the encapsulation efficiency is at least about 80%, preferably, the encapsulation efficiency is at least about 90%, more preferably at least about 95%. As used herein, the term "encapsulation efficiency" refers to the ratio of the amount of bioactive agent encapsulated in the carrier complex to the amount of bioactive agent contained in the initial solution of carrier complex and bioactive agent.

In one embodiment, the agent contained in the liposome composition of the present invention is a therapeutic agent. Due to the stability of the liposome which protects the bioactive agent, the doses can be lowered and the undesired side effects of chemotherapy can be reduced.

In another embodiment, the agent contained in the liposome composition is an anticancer entity. In one embodiment, the anticancer agent is docosahexanoic acid (DHA). The anticancer agent contained in the liposome is not limited to one cancer agent and can contain one or more anticancer agents or any other therapeutic agent. A partial listing of some of the commonly known commercially approved (or in active development) antineoplastic agents by classification is as follows.

Structure-Based Classes: Fluoropyrimidines—5-FU, Fluorodeoxyuridine, Ftorafur, 5'-deoxyfluorouridine, UFT, S-1 Capecitabine; pyrimidine Nucleosides—Deoxycytidine, Cytosine Arabinoside, 5-Azacytosine, Gemcitabine, 5-Azacytosine-Arabinoside; Purines—6-Mercaptopurine, Thioguanine, Azathioprine, Allopurinol, Cladribine, Fludarabine, Pentostatin, 2-Chloro Adenosine; Platinum Analogues—Cisplatin, Carboplatin, Oxaliplatin, Tetraplatin, Platinum-DACH, Ormaplatin, CI-973, JM-216; Anthracyclines/Anthracenediones—Doxorubicin, Daunorubicin, Epirubicin, Idarubicin, Mitoxantrone; Epipodophyllotoxins—Etoposide, Teniposide; Camptothecins—Irinotecan, Topotecan, Lurtotecan, Silatecan, 9-Amino Camptothecin, 10,11-Methylenedioxy Camptothecin, 9-Nitro Camptothecin, TAS103, 7-(4-methyl-piperazino-methylene)-10,11-ethylenedioxy-20(S)-camptothecin, 7-(2-N-isopropylamino)ethyl)-20(S)-camptothecin; Hormones and Hormonal Analogues—Diethylstilbestrol, Tamoxifen, Toremefine, Tolmudex, Thymitaq, Flutamide, Bicalutamide, Finasteride, Estradiol, Trioxifene, Droloxifene, Medroxyprogesterone Acetate, Megesterol Acetate, Aminoglutethimide, Testolactone and others; Enzymes, Proteins and Antibodies—Asparaginase, Interleukins, Interferons, Leuprolide, Pegaspargase, and others; Vinca Alkaloids—Vincristine, Vinblastine, Vinorelbine, Vindesine; Taxanes—Paclitaxel, Docetaxel.

Mechanism-Based Classes: Hormones and Hormonal Analogues, Anastrozole; Antifolates—Methotrexate, Aminopterin, Trimetrexate, Trimethoprim, Pyritrexim, Pyrimethamine, Edatrexate, MDAM; Antimicrotubule Agents—Taxanes and Vinca Alkaloids; Alkylating Agents (Classical and Non-Classical)-Nitrogen Mustards (Mechlorethamine, Chlorambucil, Melphalan, Uracil Mustard), Oxazaphosphorines (Ifosfamide, Cyclophosphamide, Perfosfamide, Trophosphamide), Alkylsulfonates (Busulfan), Nitrosoureas (Carmustine, Lomustine, Streptozocin), Thiotepa, Dacarbazine and others; Antimetabolites—Purines, pyrimidines and nucleosides, listed above; Antibiotics—Anthracyclines/Anthracenediones, Bleomycin, Dactinomycin, Mitomycin, Plicamycin, Pentostatin, Streptozocin; topoisomerase Inhibitors—Camptothecins (Topo I), Epipodophyllotoxins, m-AMSA, Ellipticines (Topo II); Antivirals—AZT, Zalcitabine, Gemcitabine, Didanosine, and others; Miscellaneous Cytotoxic Agents—Hydroxyurea, Mitotane, Fusion Toxins, PZA, Bryostatin, Retinoids, Butyric Acid and derivatives, Pentosan, Fumagillin, and others.

In addition to the above, an anticancer entity include without any limitation, any topoisomerase inhibitor, vinca alkaloid, e.g., vincristine, vinblastine, vinorelbine, vinflunine, and vinpocetine, microtubule depolymerizing or destabilizing agent, microtubule stabilizing agent, e.g., taxane, aminoalkyl or aminoacyl analog of paclitaxel or docetaxel, e.g., 2'-[3-(N,N-Diethylamino)propionyl]paclitaxel, 7-(N,N-Dimethylglycyl)paclitaxel, and 7-L-alanylpaclitaxel, alkylating agent, receptor-binding agent, tyrosine kinase inhibitor, phosphatase inhibitor, cycline dependent kinase inhibitor, enzyme inhibitor, aurora kinase inhibitor, nucleotide, polynucleotide, and farnesyltransferase inhibitor.

In another embodiment, the agent contained in the liposome composition of the present invention is a therapeutic agent of anthracycline compounds or derivatives, camptothecine compounds or derivatives, ellipticine compounds or derivatives, vinca alkaloinds or derivatives, wortmannin, its analogs and derivatives, or pyrazolopyrimidine compounds with the aurora kinase inhibiting properties.

In yet another embodiment, the agent contained in the liposome composition of the present invention is an anthracycline drug, doxorubicin, daunorubicin, mitomycin C, epirubicin, pirarubicin, rubidomycin, carcinomycin, N-acetyladriamycin, rubidazone, 5-imidodaunomycin, N-acetyldaunomycine, daunoryline, mitoxanthrone; a camptothecin compound, camptothecin, 9-aminocamptothecin, 7-ethylcamptothecin, 10-hydroxycamptothecin, 9-nitrocamptothecin, 10,11-methylenedioxycamptothecin, 9-amino-10,11-methylenedioxycamptothecin, 9-chloro-10,11-methylenedioxycamptothecin, irinotecan, topotecan, lurtotecan, silatecan, (7-(4-methylpiperazinomethylene)-10,11-ethylenedioxy-20(S)-camptothecin, 7-(4-methylpiperazinomethylene)-10,11-methylenedioxy-20(S)-camptothecin, 7-(2-N-isopropylamino)ethyl)-(20S)-camptothecin; an ellipticine compound, ellipticine, 6-3-aminopropyl-ellipticine, 2-diethylaminoethyl-ellipticinium and salts thereof, datelliptium, retelliptine.

In yet another embodiment, the agent contained in the liposome of the present invention is a pharmaceutical entity including, without limitation any of the following: antihistamine ethylenediamine derivatives (bromphenifamine, diphenhydramine); Anti-protozoal: quinolones (iodoquinol); amidines (pentamidine); antihelmintics (pyrantel); antischistosomal drugs (oxaminiquine); antifungal triazole derivatives (fliconazole, itraconazole, ketoconazole, miconazole); antimicrobial cephalosporins (cefazolin, cefonicid, cefotaxime, ceftazimide, cefuoxime); antimicrobial beta-lactam derivatives (aztreopam, cefmetazole, cefoxitin); antimicrobials of erythromycine group (erythromycin, azithromycin, clarithromycin, oleandomycin); penicillins (benzylpenicillin, phenoxymethylpenicillin, cloxacillin, methicillin, nafcillin, oxacillin, carbenicillin); tetracyclines; other antimicrobial antibiotics, novobiocin, spectinomycin, vancomycin; antimycobacterial drugs: aminosalicycic acid, capreomycin, ethambutol, isoniazid, pyrazinamide, rifabutin, rifampin, clofazime; antiviral adamantanes: amantadine, rimantadine; quinidine derivatives: chloroquine, hydroxychloroquine, promaquine, qionone; antimicrobial qionolones: ciprofloxacin, enoxacin, lomefloxacin, nalidixic acid, norfloxacin, ofloxacin; sulfonamides; urinary tract antimicrobials: methenamine, nitrofurantoin, trimetoprim; nitroimidazoles: metronidazole; cholinergic quaternary ammonium compounds (ambethinium, neostigmine, physostigmine); anti-Alzheimer aminoacridines (tacrine); anti-Parkinsonal drugs (benztropine, biperiden, procyclidine, trihexylhenidyl); anti-muscarinic agents (atropine, hyoscyamine, scopolamine, propantheline); adrenergic dopamines (albuterol, dobutamine, ephedrine, epinephrine, norepinephrine, isoproterenol, metaproperenol, salmetrol, terbutaline); ergotamine derivatives; myorelaxants or curane series; central action myorelaxants; baclophen, cyclobenzepine, dentrolene; nicotine; beta-adrenoblockers (acebutil, amiodarone); benzodiazepines (ditiazem); antiarrhythmic drugs (diisopyramide, encaidine, local anesthetic series—procaine, procainamide, lidocaine, flecaimide), quinidine; ACE inhibitors: captopril, enelaprilat, fosinoprol, quinapril, ramipril; antilipidemics: fluvastatin, gemfibrosil, HMG-coA inhibitors (pravastatin); hypotensive drugs: clonidine, guanabenz, prazocin, guanethidine, granadril, hydralazine; and non-coronary vasodilators: dipyridamole.

Oligonucleotides:

In preferred embodiments, the bioactive agent comprises oligonucleotides specific for molecules associated with cancer, autoimmunity, diabetes, inflammation, neurological disorders, infectious agents and the like. The term "oligonucleotide," is meant to encompass all forms or desired RNA, RNA/DNA molecules, and includes without limitation: "siRNA," "shRNA" "antisense oligonucleotide", interference RNA etc. The term also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoogsteen or reverse Hoogsteen types of base pairing, or the like.

In another preferred embodiment, the oligonucleotide comprises one or more nucleotide substitutions. Preferably, the nucleotide substitutions comprise at least one or combinations thereof, of adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$-$C^6$)-alkynylcytosine, 5-fluorouracil, 5-bromouracil, pseudoisocytosine, 2-hydroxy-5-methyl-4-triazolopyridin, isocytosine, isoguanin, inosine, non-naturally occurring nucleobases, locked nucleic acids (LNA), peptide nucleic acids (PNA), variants, mutants and analogs thereof.

The specificity of oligonucleotides is limited only by the imagination of the user and are to a wide range of diseases or disorders. These oligonucleotides can be used in the prevention or treatment of infectious disease organisms, parasites, viruses, bacteria, and the like. In other aspects immune suppression may be desired, for example, inflammation, autoimmunity, transplantation and the like. In others a strong memory induction is need as in the case, for example, tumors, infections and the like.

One aspect of the invention comprises a pharmaceutical composition in combination with other treatments for which the bioactive agents are used. For example, in inflammatory, infectious organisms, autoimmune diseases, cancer, and other related disorders, the appropriate therapeutic care can be conducted in parallel or concomitantly. Examples: chemotherapy, radiation therapy, antibiotics, anti-inflammatory agent, an immunostimulator, an antiviral agent, or the like. Furthermore, the compositions of the invention may be administered in combination with a cytotoxic, cytostatic, or chemotherapeutic agent such as an alkylating agent, antimetabolite, mitotic inhibitor or cytotoxic antibiotic, as described above. In general, the currently available dosage forms of the known therapeutic agents for use in such combinations will be suitable.

In another preferred embodiment, the liposomes comprising an oligonucleotide are administered to patients in need of a transplant. The oligonucleotides can be specific for one or more molecules associated with immune cell responses and regulatory pathways thereof.

Polypeptides:

In some embodiments, the bioactive agent is a polypeptide. In one embodiments, the polypeptide is insulin, or pro-insulin.

In a further aspect, the present invention provides a use of a liposome comprising a pharmaceutical composition according to the invention for treatment or prevention of a disorder selected from a group consisting of: type II diabetes, insulin resistance, impaired glucose intolerance, hyperglycemia, hyperlipidaemia, hyperinsulinemia, impaired glucose metabolism, obesity, diabetic retinopathy, diabetic nephropathy, glomerulosclerosis, syndrome X, hypertension, heart disease, cardiovascular disease, stroke, endothelial dysfunction, congestive heart failure, angina, peripheral arterial disease, chronic renal failure, and acute renal failure.

In a further aspect, the present invention provides a method of treating or inhibiting a disorder selected from a group consisting of: type II diabetes, insulin resistance, impaired glucose intolerance, hyperglycemia, hyperlipidaemia, hyperinsulinemia, impaired glucose metabolism, obesity, diabetic retinopathy, diabetic nephropathy, glomerulosclerosis, syndrome X, hypertension, heart disease, cardiovascular disease, stroke, endothelial dysfunction, congestive heart failure, angina, peripheral arterial disease, chronic renal failure, and acute renal failure, comprising administering a therapeutically effective amount of liposomes encapsulating a pharmaceutical composition according to an embodiment of the invention.

In a further aspect, the present invention provides a method of treating or inhibiting a disorder selected from a group consisting of: type II diabetes, insulin resistance, impaired glucose intolerance, hyperglycemia, hyperlipidaemia, hyperinsulinemia, impaired glucose metabolism, obesity, diabetic retinopathy, diabetic nephropathy, glomerulosclerosis, syndrome X, hypertension, heart disease, cardiovascular disease, stroke, endothelial dysfunction, congestive heart failure, angina, peripheral arterial disease, chronic renal failure, and acute renal failure, comprising administering a therapeutically effective amount of insulin and/or one or more of a therapeutically effective amount at least one diabetes drug.

As used herein, the term "diabetes drug" refers to any composition known in the art to be useful in the treatment or prevention of insulin resistance and diabetes. Examples of diabetes drugs which may be used to practice the invention include, but are not limited to: an antioxidant such as vitamin E, vitamin C, an isoflavone, zinc, selenium, ebselen, a carotenoid; an insulin or insulin analogue such as regular insulin, lente insulin, semilente insulin, ultralente insulin, NPH, HUMALOG™, or NOVOLOG™; an α-adrenergic receptor antagonist such as prazosin, doxazocin, phenoxybenzamine, terazosin, phentolamine, rauwolscine, yohimine, tolazoline, tamsulosin, or terazosin; a β-adrenergic receptor antagonist such as acebutolol, atenolol, betaxolol, bisoprolol, carteolol, esmolol, metoprolol, nadolol, penbutolol, pindolol, propranolol, timolol, dobutamine hydrochloride, alprenolol, bunolol, bupranolol, carazolol, epanolol, moloprolol, oxprenolol, pamatolol, talinolol, tiprenolol, tolamolol, or toliprolol; a non-selective adrenergic receptor antagonist such as carvedilol or labetolol; a first generation sulphonylurea such as tolazamide, tolubtuamide, chlorpropamide, acetohexamide; a second generation sulphonylurea such as glyburide, glipizide, and glimepiride; a biguanide agent such as is metformin; a benzoic acid derivative such as repaglinide; an α-glucosidase inhibitor such as acarbose and miglitol; a thiazolidinedione such as rosiglitazone, pioglitazone, or troglitazone; a phosphodiesterase inhibitor such as anagrelide, tadalfil, dipyridamole, dyphylline, vardenafil, cilostazol, milrinone, theophylline, or caffeine; a cholinesterase antagonist such as donepezil, tacrine, edrophonium, demecarium, pyridostigmine, zanapezil, phospholine, metrifonate, neostigmine, or galanthamine; and a glutathione increasing compound such as N-acetylcysteine, a cysteine ester, L-2-oxothiazolidine-4-carboxylate (OTC), gamma glutamylcysteine and its ethyl ester, glytathtione ethyl ester, glutathione isopropyl ester, lipoic acid, cysteine, methionine, bucillamine or S-adenosylmethionine; GLP and glucagon like peptide analogues, such as exanitide, DAC:GLP-1(CJC-1131), Liraglutide, ZP10, BIM51077, LY315902, LY307161 (SR).

According to the present invention, the agent contained in the liposome composition of the present invention can also be a pro-drug or an agent that is capable of being converted to a desired agent upon one or more conversion steps under a condition such as a change in pH or an enzymatic cleavage of a labile bond. Such conversion may occur after the release of the pro-drug from the liposome interior at the intended site of the drug/liposome action. However, the agent can be converted into the desired active entity inside the liposomes of the present invention prior to the use of the liposomes as a delivery vehicle, e.g., administration to a patient. For example, an agent can be modified so that it is easier to be loaded into the liposomes. In this manner, according to the present invention, the agents that are generally not amenable to "active", "remote" or other gradient-based loading methods, can be effectively loaded into liposomes, e.g., into the liposome interior space, in their native, unmodified form.

One of ordinary skill in the art can employ various known methods to modify the agent. For example, globally cationic compounds, that is, compounds capable of attaining a net positive ionic charge under the liposome loading conditions, especially the compounds containing a titratable amine, effectively load into liposomes exhibiting transmembrane ion gradients. If an entity of interest is an organic compound and is not a globally cationic compound having a titratable amine, a derivative thereof having the requisite ionic properties can be prepared by a suitable modification. For example, an amine group can be introduced by esterification of a hydroxyl group of the entity with an amino acid. Alternatively, a hydrophobic group can be introduced into a water-soluble compound to aid in its partition into the liposome membrane and subsequent traversing of the membrane to the intraliposomal compartment, i.e., inside the liposomes. Another useful modification to create a liposome-loadable agent is the formation of a carbonyl group adduct, e.g., a hydrazone, an oxime, an acetal, or a ketal. A modified amino-containing group can be hydrolyzed or otherwise chemically split from the modified compound after the loading of the modified compound into the liposomes according to the present invention. Typical processes to intraliposomally regenerate the entity from an agent are hydrolysis, photolysis, radiolysis, thiolysis, ammonolysis, reduction, substitution, oxidation, or elimination. These processes can be affected, without limitation, by the change of pH or by an enzymatic action. In another example, paclitaxel or docetaxel, a non-ionic entities, are converted into their 2'-(diethylaminopropionyl)- or 7'-(diethylaminopropionyl) esters, which are weak bases. After loading into the liposomes by any known method, including, without limitation, "active", "remote", "transmembrane-gradient-based" or "solubility gradient based" methods, and/or the methods of the present invention, the intraliposomal 2'-(diethylaminopropionyl)-paclitaxel is converted into original paclitaxel by stimulating its hydrolysis through the increase of pH to above pH 7.0. Thus, a liposome encapsulating a neutral taxane molecule within its interior space is obtained with the drug/lipid ratio of over 0.05 mole per mole of the liposome lipid, without the help of hydrophilic covalent modifications of the taxane molecule (e.g. by attachment of PEG), cyclodextrine taxane complexes, or taxane-solubilizing, micelle-forming surfactants.

According to the present invention, the liposomes can also be targeting liposomes, e.g., liposomes containing one or more targeting moieties or biodistribution modifiers on the surface of the liposomes. A targeting moiety can be any agent that is capable of specifically binding or interacting with a desired target. In one embodiment, a targeting moiety is a ligand. The ligand, according to the present invention, preferentially binds to and/or internalizes into, a cell in which the liposome-entrapped entity exerts its desired effect (a target cell). A ligand is usually a member of a binding pair where the second member is present on or in a target cells or in a tissue comprising the target cell. Examples of ligands suitable for the present invention are: the folic acid, protein, e.g., transferrin, growth factor, enzyme, peptide, receptor, antibody or antibody fragment, such as Fab', Fv, single chain Fv, single-domain antibody, or any other polypeptide comprising antigen-binding sequences (CDRs) of an antibody molecule. A ligand-targeted liposome wherein a targeting moiety is an antibody or a target antigen-binding fragment thereof is called an immunoliposome. In a preferred embodiment, the liposome carrying a targeting moiety, e.g., a ligand, is internalized by a target cell. In yet another embodiment, a targeting moiety is a ligand that specifically interacts with a tyrosine kinase receptor such as, for example, EGFR, HER2, HER3, HER4, PD-GFR, VEGFR, bFGFR or IGFR receptors. In one embodiment, the targeting ligand specifically binds to Her2/neu markers. In still another embodiment, the targeting moiety specifically interacts with a growth factor receptor, an angiogenic factor receptor, a transferrin receptor, a cell adhesion molecule, or a vitamin receptor.

According to yet another embodiment of the present invention, the liposome composition of the present invention can be provided in a kit comprising a container with the liposomes, and optionally, a container with the entity and an instruction, e.g., procedures or information related to using the liposome composition in one or more applications. Such instruction can be provided via any medium, e.g., hard paper copy, electronic medium, or access to a database or website containing the instruction.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compositions of the present invention and practice the claimed methods. The following working examples therefore, specifically point out the preferred embodiments of the present invention, and are not to be construed as limiting in any way the remainder of the disclosure.

Example 1: Development of an Acid Stable Liposomal Formulation of Docosahexaenoic Acid Materials and Methods A liposomal formulation was developed having a molar ratio of 6:3:1 1,2-di-O-hexadecyl-sn-glycero-3-phosphatidylcholine, 1,2-di-O-phytanyl-sn-glycero-3-phosphatidylethanolamine, and DHA sodium salt (FIG. 1). These liposomes were made by drying the lipid solution and DHA sodium salt under nitrogen for four hours, followed by rehydration in one milliliter of 0.9% degassed saline solution. The liposomes were then heated at a temperature of 60° C. for a duration of an hour and a half, while sonicating every fifteen minutes. To ensure a homogenous distribution in size, the liposomal solution was manually extruded thirteen times through a 0.1 μm membrane with an Avanti Extruder at 60° C. Finally, the liposomes were columned through CL4B beads to remove any excess DHA that was not encapsulated and submitted to mass spectroscopy.

Results

Figure 2:
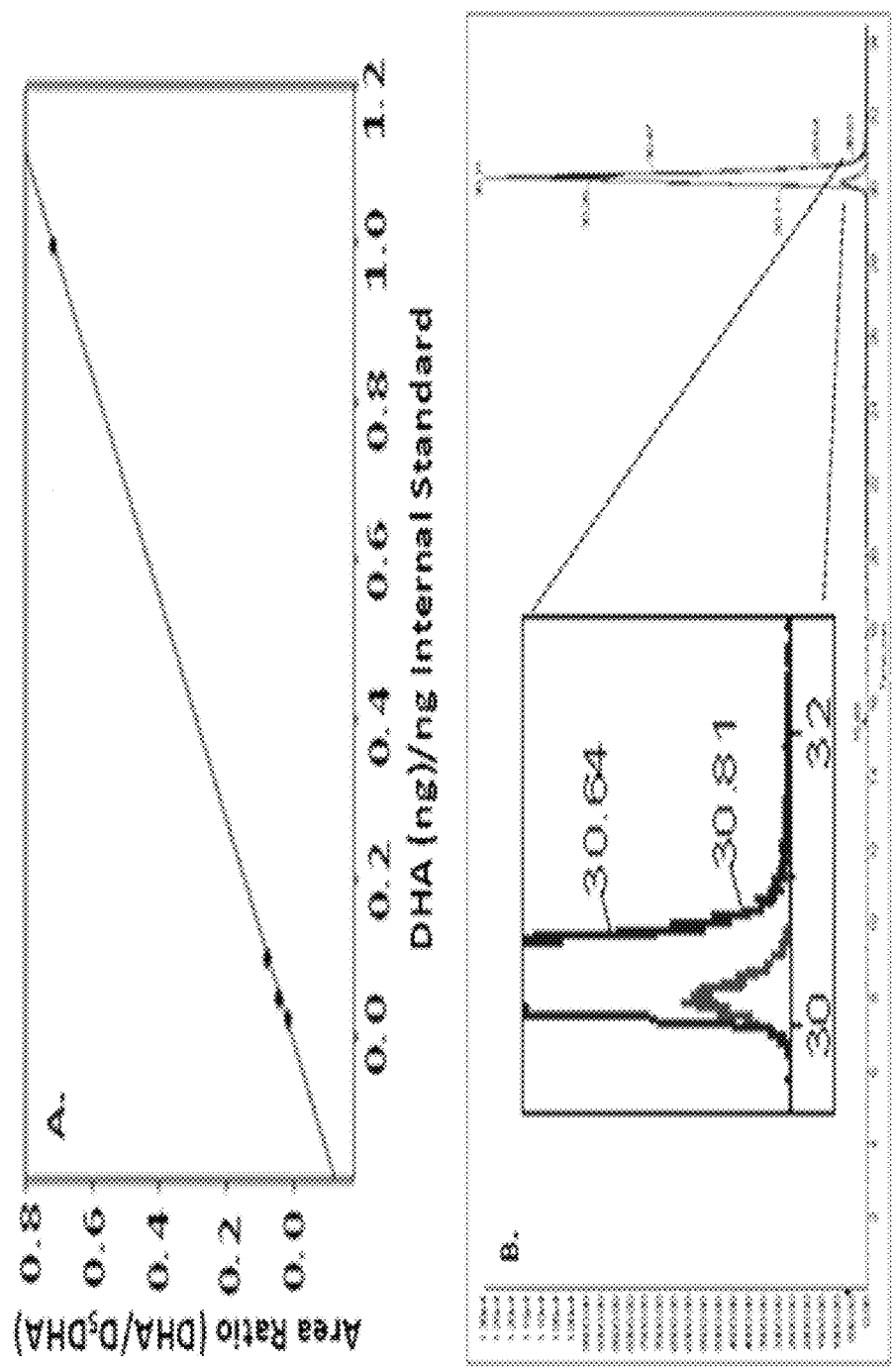
FIG. 2A is a graph showing the standard curve of DHA.
FIG. 2B is a graph showing the HPLC chromatography of DHA ether liposome.

The Determination of Encapsulation Efficiency by Liquid Chromatography Mass Spectroscopy:

Through LC-MS/MS the encapsulation efficiency of DHA was shown to be around 80% (FIG. 2).

Figure 3:
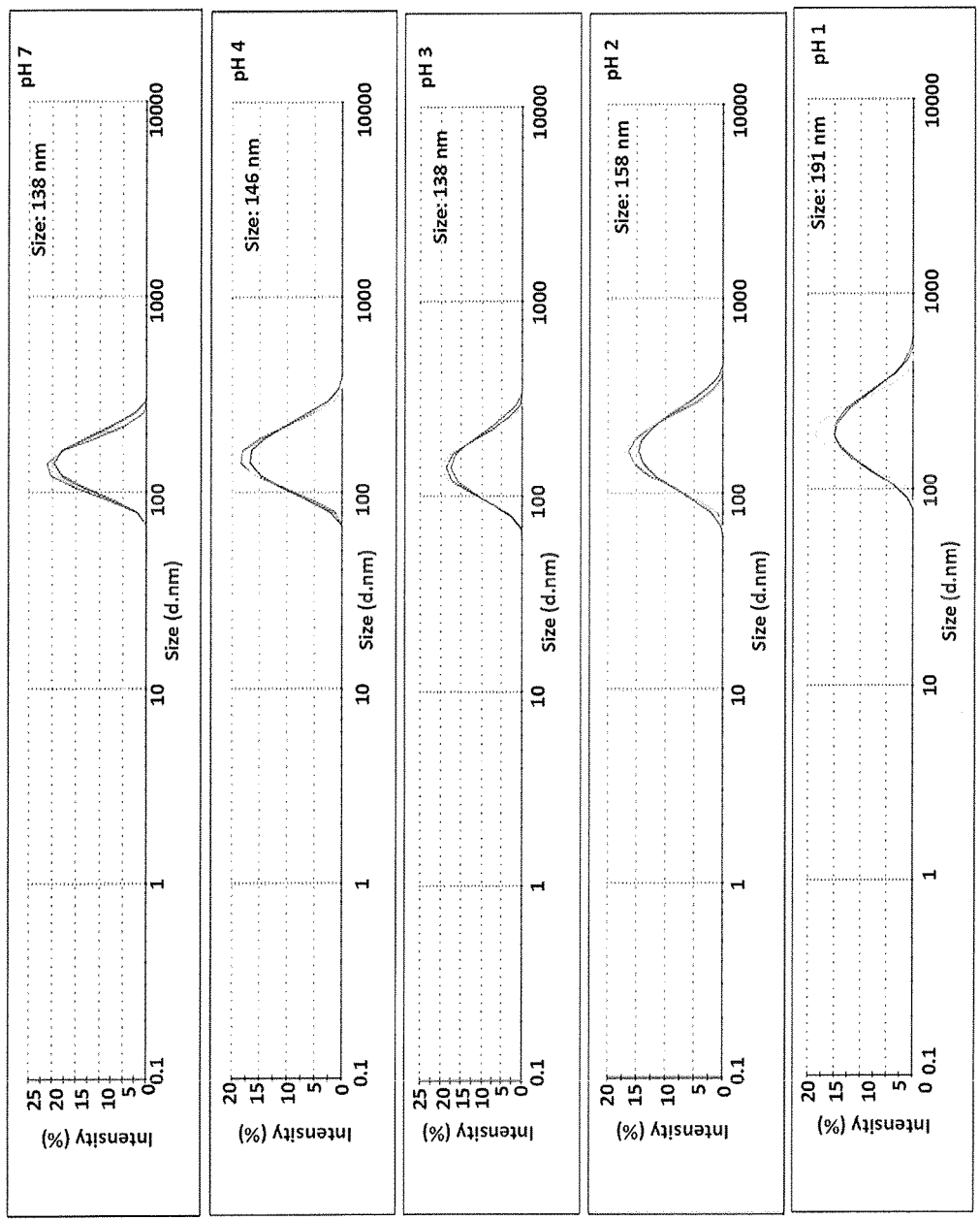
FIG. 3 is a set of graphs showing the dynamic light scattering of liposomal DHA at various pHs at room temperature.

The Determination of the Size of the Liposome at Various pH's by Dynamic Light Scattering:

The average size of the ether liposomes, determined by Dynamic Light Scattering, is around 130 nm and encompasses a negative zeta potential. This size allows for them to be ideal for oral administration, since it is known that latex particles less than 200 nm can cross into the enterocytes of the intestine. Experiments observing the effects of pH have been conducted to evaluate the ether liposomal formulation in acidic conditions. FIG. 3 illustrates that the ether liposome formulation is stable from pH 1-7 ranging in diameter from 133.8 nm to 191 nm.

The ether liposome formulation was also shown to be stable at pH 1 at 37° C. and ranged in size from 137.3 nm to 160 nm.

Figure 4:
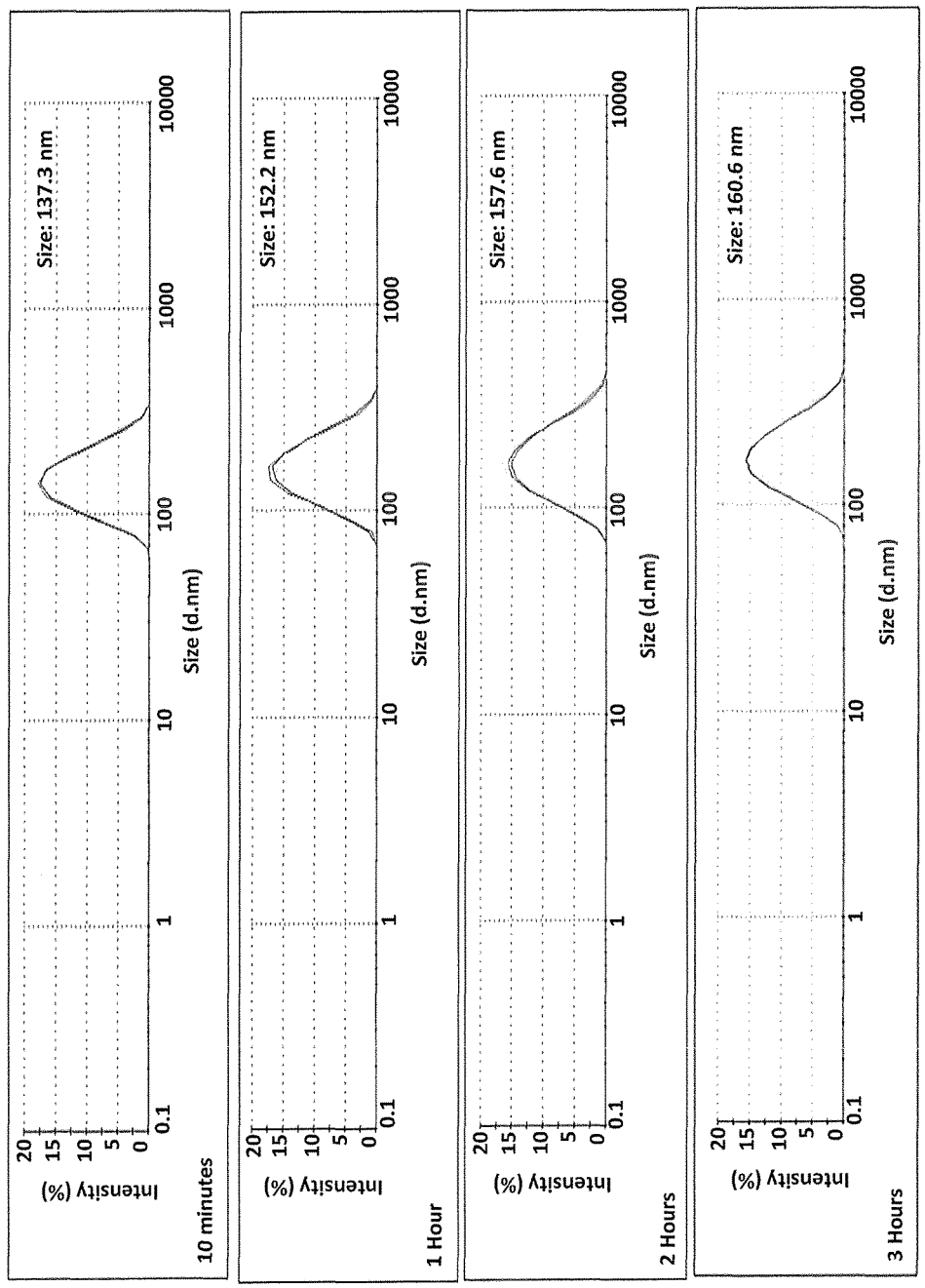
FIG. 4 is a set of graphs showing the dynamic light scattering of liposomal DHA at pH 1 and at 37° C.
Figure 5:
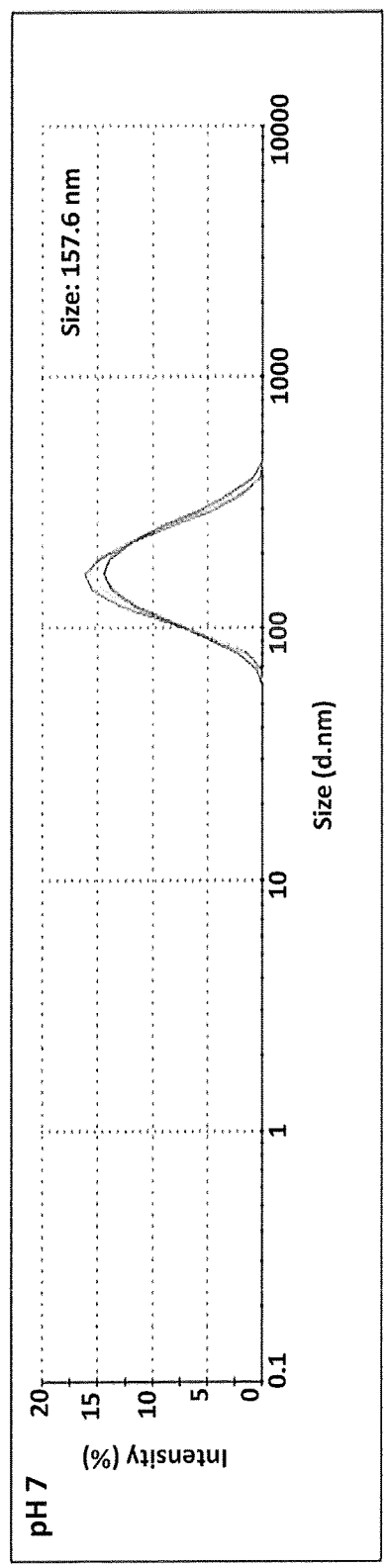
FIG. 5 is a graph showing the dynamic light scattering of a ghost liposome, i.e., a liposome having the same lipid composition as insulin-ORAL or DHA-ORAL, but having no bioactive agent.

Furthermore, the ghost liposome was found to be stable at pH 7 at a size of 157.6 nm (FIG. 4).

Figure 6:
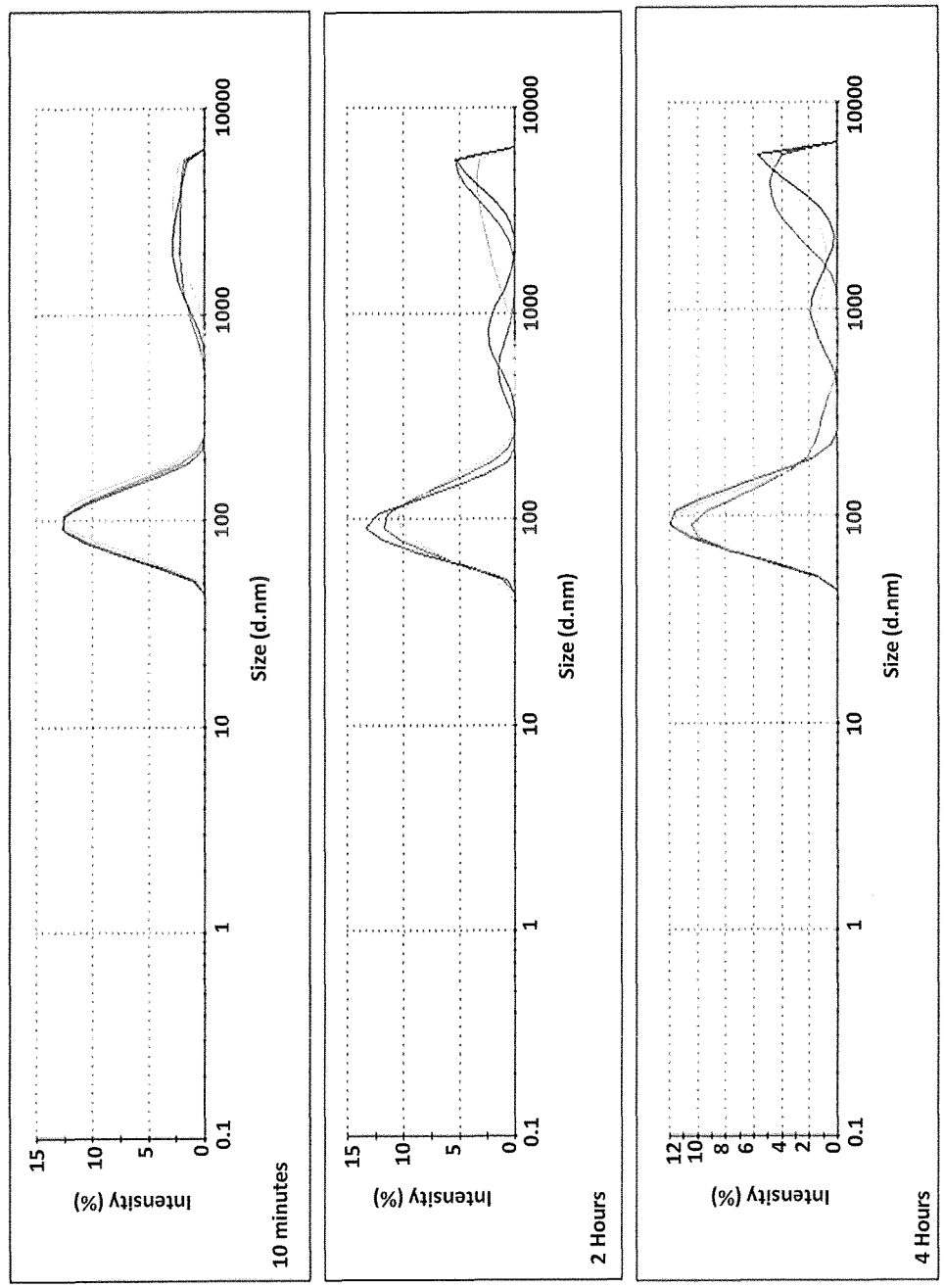
FIG. 6 is a set of graphs showing that the dynamic light scattering of conventional DHA liposomes is unstable at pH 3 and room temperature.

In comparison, the ester-based conventional liposomes containing DHA sodium salt have shown less success at maintaining size stability at pH 3 (FIG. 6), thus the ether lipids have an advantage at being more competent than conventional lipids with regards to stability in acidic conditions.

Stability of the Liposome Over Time.

Figure 7:
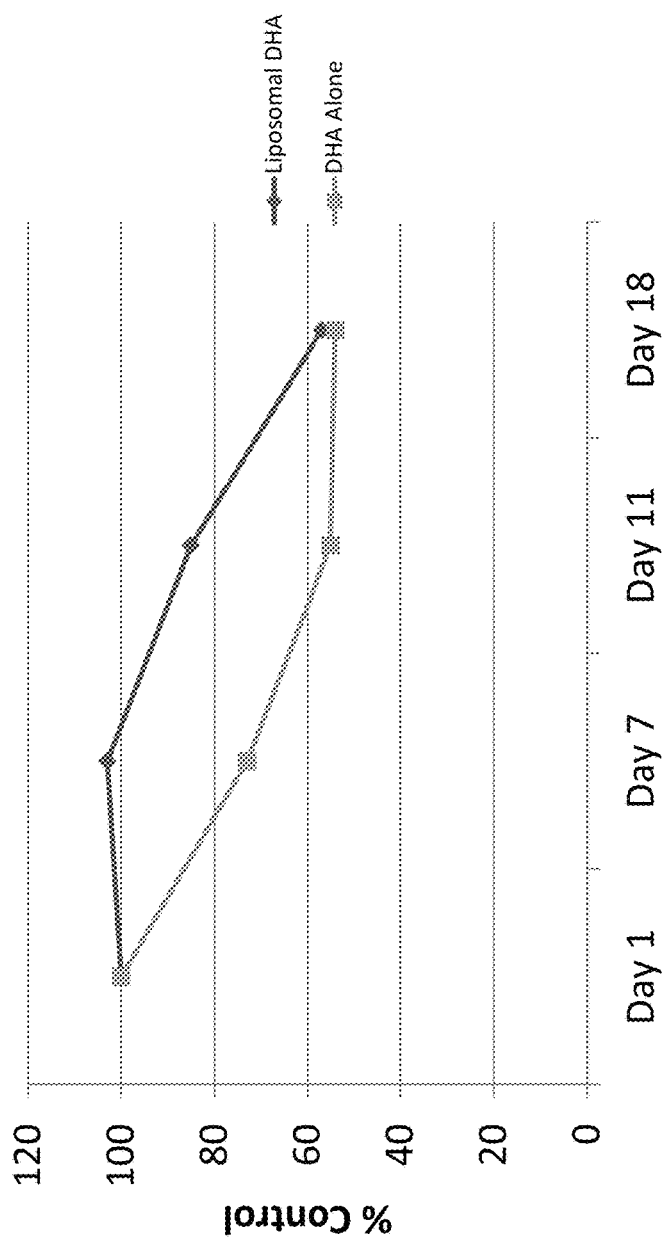
FIG. 7 is a graph showing that liposomal DHA is efficient at protecting DHA from oxidation.

Referring to FIG. 7, the graph demonstrates that liposomal DHA is efficient at protecting DHA from oxidation. The results are from a LC-MS/MS analysis of Liposomal DHA and DHA alone (in ethanol) at the various time points at 4° C. Each value for each time point is compared to the value for liposomal DHA or DHA alone on day 1, which is the control. A percentage of this was graphed to demonstrate the stability of liposomal DHA in comparison to DHA alone.

Cell Growth Inhibition Ability of this Formulation.

Figure 8:
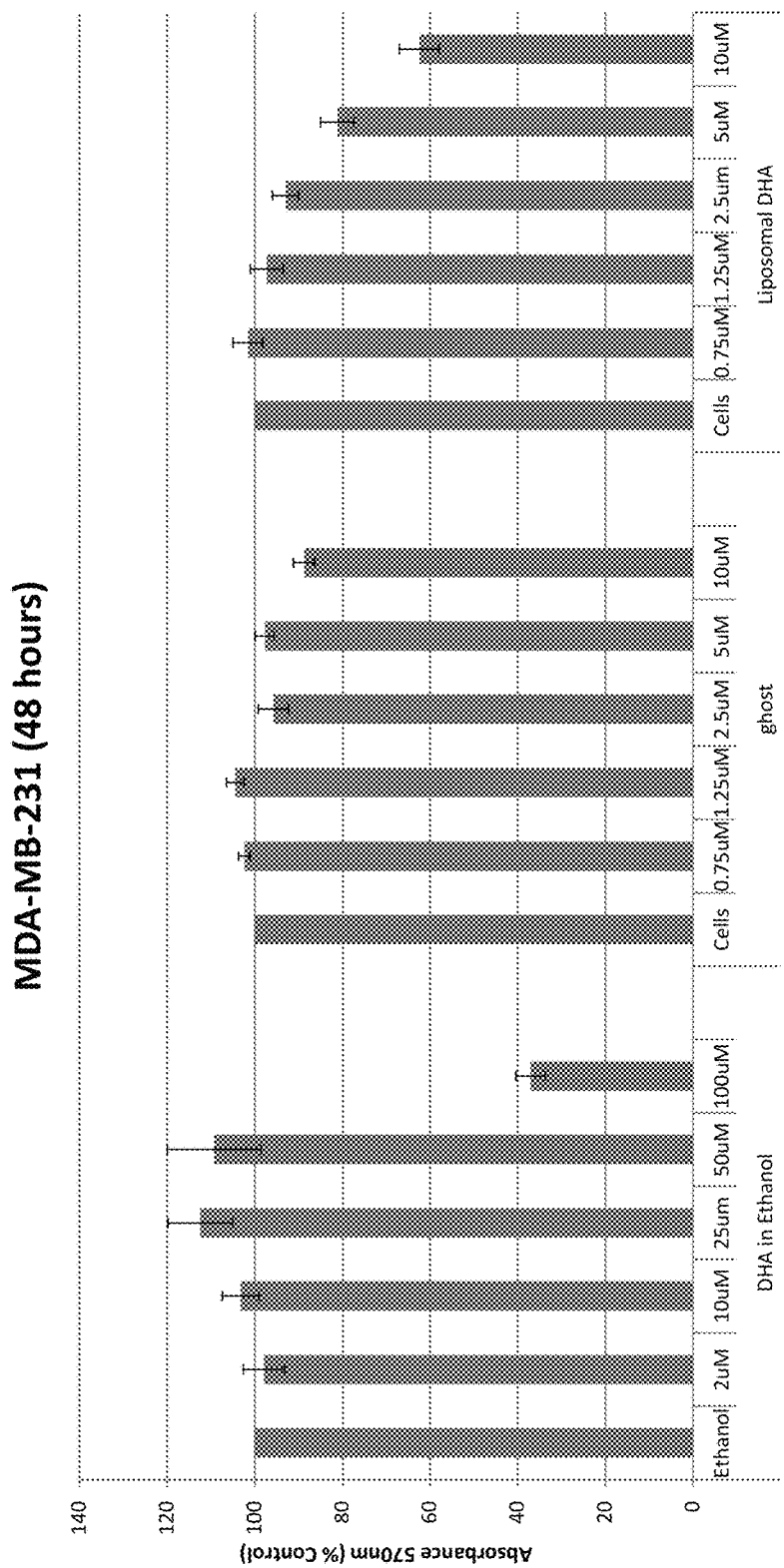
FIG. 8 is graph showing that lower amounts of liposomal DHA (5 μM-10 μM) are more efficacious at reducing cell viability than a higher amount of DHA alone (25 μM-50 μM).
Figure 9:
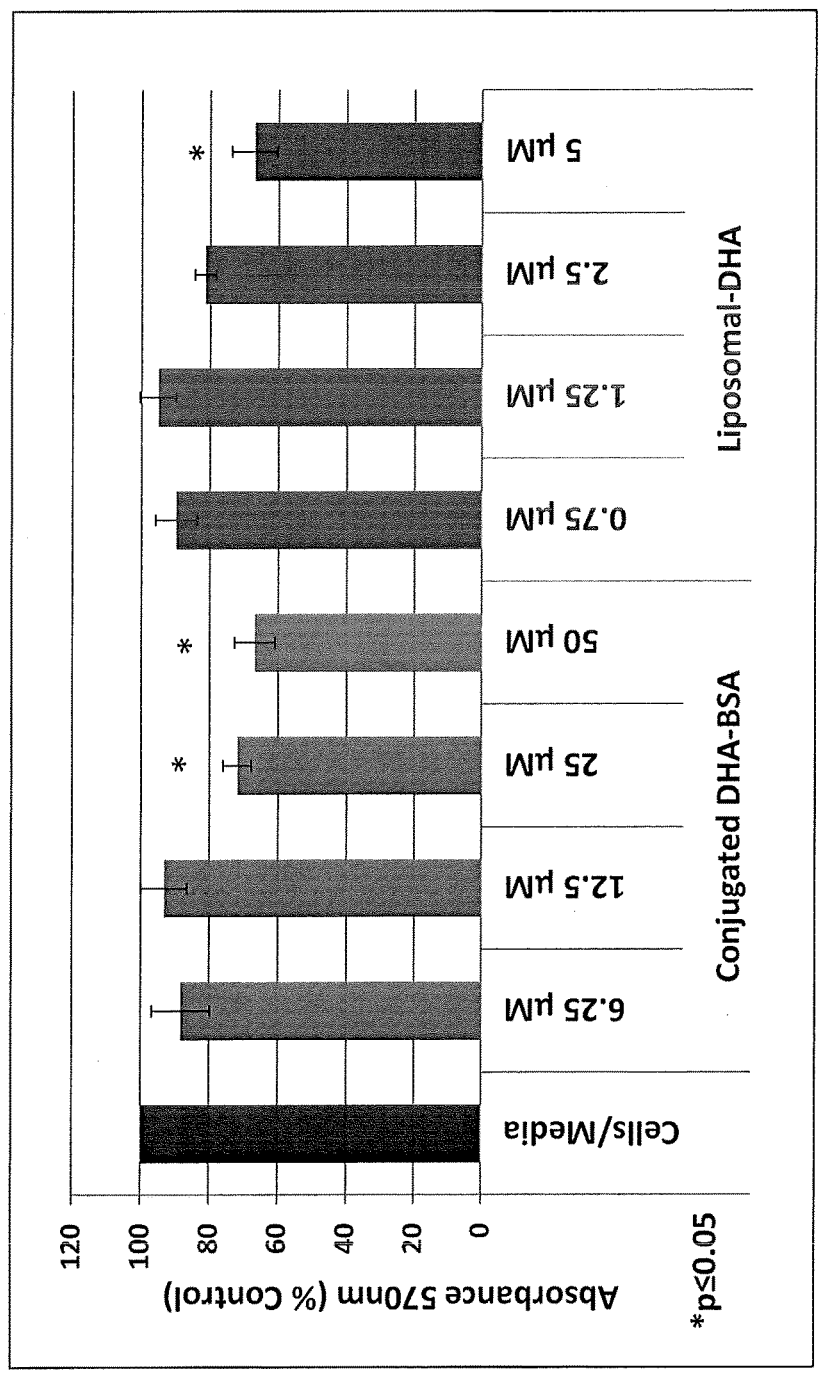
FIG. 9 is a graph showing the pH-resistant liposomes that encapsulate DHA at 5 μM inhibits cell growth using triple negative breast cancer cells while comparable effects were achieved using DHA at doses 25-50 μM. MDA-MB-231 cells were plated on a 96-well plate at 10,000 cells per well to evaluate the effects of BSA alone, conjugated DHA-BSA, Liposomal DHA, and a ghost liposome on cell viability. The cells were re-treated every 48 hours. The graph illustrates that 5 μm of liposomal DHA had a similar effect on cell viability as 25 μm conjugated DHA-BSA. All treatments were compared to the cell/media control. The ghost had no effect on cell viability.

Experiments were performed to evaluate the cell growth inhibition ability of this formulation in in-vitro breast cancer cell lines (MCF-7, MDA-MB-231). For example, MDA-MB-231 cells were plated on a 96-well plate at 6000 cells per well to evaluate the effects of DHA alone, liposomal DHA, and a ghost liposome on cell viability. The cells were plated for 24 hours followed by treatment with the DHA alone, liposomal DHA, and a ghost liposome for 48 hours. Liposomal DHA and the ghost liposome were compared to the cell/media control, while DHA alone was compared to an ethanol control. The results are shown in FIG. 8, demonstrating that lower amounts of liposomal DHA (5 μM-10 μM) are more efficacious at reducing cell viability than a higher amount of DHA alone (25 μM to 50 μM). The experiment above was a combination of two MTT assays with the same conditions.

In addition, the apoptotic induction effect and certain proteins known to be important in the cancer preventive pathways influenced by DHA can be investigated. For example, pharmacokinectic studies and chemopreventive efficacy studies in Sprague-Dawley rats can be performed using the liposomes once an effective dose of the liposomes is determined using standard methods known in the art.

Example 2: Liposomes for Intravenous Formulations of Hydrophobic and Hydrophilic Agents These drug delivery vehicles offer protection of agents from metabolism or degradation, protection against precipitation in biological fluids, enhanced biological half-life, improved pharmacokinetic properties, improved water solubility and enhanced membrane permeability. The utility of liposomal delivery has been improved by the use of PEGylated lipid structures as well as homogeneous nanosizing (<100 nm) that serve to evade the reticuloendothelial system. However, the utility of liposomes as orally administered drug delivery vehicles has been hampered by the lack of these lipid-based systems to withstand the acid environment of the stomach.

To address this limitation of liposomes, a pH-resistant nanoliposome was developed that is structurally intact at a pH as low as 1. (See Example 1). Lipids that can withstand an environment of high acidity and temperature are ideal for an orally administered liposome and have been discovered in organisms that have evolved to thrive in these hostile environments. As an example, archaeobacteria is an organism that is composed of unique membrane lipids that contain saturated alkyl chains with methyl branching attached to glycerol by ether linkages. The ether linkages of these lipids are stable over a variety of temperatures and acidic pHs and are more resistant to attack by acid-regulated phospholipases than traditional ester-based lipids. The branched methyl groups provide a strategy to reduce membrane leakage and increase stability at low pH.

Therefore, to develop liposomes that provide protection from fluctuations in pH based upon lipids found in archaeobacteria, commercially available ether lipids 1,2-di-O-hexadecyl-sn-glycero-3-phosphatidylcholine, 1,2-di-O-phytanyl-sn-glycero-3-phosphatidylethanolamine, and 1,2-di-O-phytanyl-sn-glycero-3-phosphatidylcholine were utilized. These ether lipids contain ether bonds and methyl branching, both characteristics of archaeol lipids. A liposome containing these lipids is less susceptible to phospholipase hydrolysis and changes in pH.

Insulin is a polypeptide that is administered intramuscularly and must be carefully monitored and timed. Moreover, dosage must be tightly controlled and monitored as a consequence of diet. The costs and difficulties of active glucose monitoring are escalating, especially in third world countries, due to changes in traditional diets and the onset of Type "$1_{1/2}$" diabetes. Oral administration would offer the advantages of ease of use, less pain, compliance, and cost containment. Moreover, protection of the active from metabolism and clearance by "nanosizing" within pH-resistant liposomes could significantly improve efficacy, utility and safety. Despite the use of more acid-stable and peptidase-stable insulin formulations, oral administration is still an underdeveloped concept, compared to current injectable and pump technologies.

A DHA (docahexaenoic acid) intercalated ether-lipid based liposome was formulated. DHA (22:6 n-3), a component in fish oil, has been evaluated in preclinical models and has shown to be the most effective of the omega-3s in the prevention of breast cancer. A formulation for oral delivery that considers pH stability and oxidative stability of DHA is expected to be superior for chemoprevention compared to non-liposomal formulations. In one embodiment, a liposomal formulation was produced comprising 1,2-di-O-hexadecyl-sn-glycero-3-phosphatidylcholine, 1,2-di-O-phytanyl-sn-glycero-3-phosphatidylethanolamine, and DHA sodium salt in a molar ratio of 6:3:1 (components of the liposome are shown in FIG. 1).

These liposomes were made by drying the lipid solution and DHA sodium salt under nitrogen for four hours, followed by rehydration in one milliliter of 0.9% degassed saline solution. The liposomes were then heated at a temperature of 60° C. for a duration of an hour and a half, while sonicating every fifteen minutes. To ensure a homogenous distribution in size, the liposomal solution was manually extruded thirteen times through a 0.1 μm membrane with a mini-Extruder at 60° C. Finally, the liposomes were columned through CL4B beads to remove any excess DHA that was not encapsulated. Preliminary HPLC and mass spectrometry data evidence encapsulation efficiency of DHA of nearly 80%. The average size of the ether liposomes, determined by Dynamic Light Scattering, is approximately 130 nm, exhibiting a −10 mV zeta potential. This size is suited for oral administration, since it is known that latex particles less than 200 nm can cross into the enterocytes of the intestine. A monodispersed size distribution of DHA ether liposomes at PHs from 7 to 1, even though the size distribution slightly expands at pH 1 and 2. Remarkably, the DHA containing pH-resistant formulations were shown to be monodispersed at pH 1 for periods up to 3 hrs. In comparison, DHA intercalated into traditional ester-based liposomes, 2:1 PC/PE (phosphatidylcholine/phosphatidylethanolamine), yielded unstable formulations at pH, exhibiting significant agglomeration over time.

Formulation and Synthesis of pH-Resistant Insulin Liposomes:

Based upon preliminary data with DHA, a 2:1 1,2 di-O-hexadecyl-sn-glycero—3-phosphocholine/1,2-di-O-phytanyl-sn-glycero-3 phosphatidylethanolamine base formulation was utilized. To improve stealth capabilities and lessen immunological and inflammatory reactions, PEGylated lipids were incorporated into the base formulation. Liposomal formulation containing up to 15 molar percent PEGylated ester-linked lipids have been formulated. Keeping the phosphatidylethanolamine lipid content at 50% of the phosphocholine content, the percentage of 1,2-di-O-phytanyl-sn-glycero-3 phosphatidylethanolamine was lowered at the expense of 1,2 di-O-hexadecy-sn-glycero-3-phosphatidylethanolamine-PEG 2000. The 1,2-di-O-phytanyl-sn-glycero-3 phosphatidylethanolamine will be PEGylated through traditional chemistry.

Briefly, once received, the lipids was dissolved in chloroform and combined in specific molar ratios. The lipid mixture was then dried under a stream of nitrogen, above the lipid transition temperature, hydrated with sterile phosphate buffered saline and sonicated until the lipids are suspended in the solution. For small scale manufacturing, the lipid solution was then extruded 11 times through a 100 nm polycarbonate membrane at temperature above the lipid transition temperature using a temperature controlled water bath.

Upon achieving a stable PEGylated ether-linked formulation, insulin (Humulin-R, Ely Lilly) can be encapsulated at therapeutic doses. Optimization of encapsulation of the active pharmacological ingredient (API) can be evaluated by mass spectrometry as a function of passive or active trapping methodologies as well as molar ratios of selected PEGylated lipids. Unlike bioactive hydrophobic lipids which can be intercalated into liposomes by passive strategies, encapsulation of hydrophilic agents may require more active strategies to achieve maximal loading efficiencies.

Active acid trapping strategies were utilized to encapsulate hydrophilic agents. Briefly, to load insulin using an active, pH-gradient method, lipids was prepared as described above, but rehydrated with sterile 10 mM ammonium sulfate buffer, pH 4. The lipid mixture was then sonicated for 1 minute followed by extrusion, as described above to form nanoliposomes. The extruded formulation was then pH adjusted to 7.4, which created a pH gradient between the bulk solution and liposomal core, and insulin was then added in various concentrations and subjected to overnight incubation at 37° C. to facilitate exchange of insulin into the liposomal core. The pH of the ammonium sulfate buffer can be varied to achieve optimal loading without degrading the insulin. If the pH gradient approach is not optimal, an alternative approach can be utilized involving solvent dilution with dialysis filtration.

A thermo-responsive trapping approach can also be used. An example is utilizing rigid temperature control to load insulin in preformed, slightly anionic ether-linked liposomes. Specifically, 1,2-di-O-hexadecyl-sn-glycero-3-phosphatidylcholine is cleaved with phospholipase D and the resulting anionic lipid is purified and assessed by chromatography and mass spectrometry. In a preferred embodiment, this anionic lipid can compose 1-15 molar percent of the formulation.

As another example, ether-linked forms of 1,2 or lyso palmitoyl phosphatidylcholine can serve as thermo-responsive lipids that have transition temperatures around 39 to 41° C. Alternatively, temperature-sensitive (N-isopropylacrylamide (NIPAAm)) monomers can also be used to facilitate trapping of insulin.

Variables that can be adjusted and tested to optimize insulin loading include the concentration of API added to the lipid mixture (for example, 1-100 ng/ml) as well as the incubation time for mixing the insulin-lipid mixture. Also, to optimize the size and mono-dispersion of the formulations, additional extrusions and/or a combination of pressure homogenization and/or sonication can be performed. Based upon DHA experiments, liposomal mean sizes of approximately 130 nm can be achieved. In one embodiment, a mean size in the range of 80-90 nm is preferred in order to maximize stealth capabilities.

The use of PEGylated lipids in the formulation leads to liposomal mean sizes of 90-100 nm with a homogenous, monodispersed distribution that did not swell or increase size as a function of pH. Formulations generated with each loading method can be purified using a Sepharose CL-B4 column to separate free drugs from encapsulated liposomes. The amount of ether-linked phosphatidylcholine (PC) and insulin can be quantified by LC-MS, prior to evaluation in QA/QC and in vivo screens. A greater than 75% insulin encapsulation as a function of loading dose is desirable.

Characterization of pH-Resistant Therapeutics Liposomes that Encapsulate Insulin:

The formulations described herein, can be further analyzed for insulin loading, stability and release kinetics. In addition, the biophysical properties of these formulations can be investigated as a function of pH, temperature, time, media and serum components. Reproducibility, QA/QC and design specs for the formulations can also be evaluated.

To quantify the concentrations of liposomal insulin, formulations can be subjected to LC-MS following purification on Sepharose CL-4B, as described above. LC-MS can be performed using a C18 separation column with acetonitrile or 10 v/o methanol/water on an Agilent 1100 system LC system coupled to a ABI 4100. These procedures have previously been used to assess the concentration of other APIs in liposomal formulations, and calibration curves to assess 5 ng/mL-50 mg/mL of each compound have been established.

Hydrodynamic size (diameter) of the liposome samples can be measured in aqueous solutions using dynamic light scattering (DLS) at 25° C. This measurement includes the intensity-weighted average diameter overall size populations (Z-avg), the polydispersity index (PdI), the volume-weighted average diameter over the major volume peak (Vol-Peak), and its percentage of the total population (Vol-Peak % Vol). A Malvern Zetasizer Nano can be used for these measurements in batch mode (i.e., without fractionation). Samples can be diluted in either PBS or saline (e.g., 154 mM NaCl), for example to a final concentration of 1 mg/mL. Additional studies can be performed to determine size distribution as a function of concentration, which can further characterization. A minimum of seven measurements should generally be taken for each sample (as is, no filtration) in a disposable low volume (polystyrene) cuvette.

A folded capillary flow cell can be used for zeta potential measurement at a voltage of 100V. The zeta potential of insulin ether-linked liposomes at 25° C. can be measured at two different concentrations. Samples should generally be diluted in 10 mM NaCl to give a 0.1 and 1 mg/mL final concentration. A minimum of ten measurements should generally be taken for each sample.

To determine stability of the liposomal encapsulated insulin, the following procedure can be used. The selected and manufactured formulation is incubated in heparinized human plasma for 0.5, 1, 2 and 4 hours at 37° C. Following incubation, formulations are subject to further purification using Sepharose CL-4B and measured for insulin mass as described above. Any significant reduction in the concentrations of liposomal insulin is generally interpreted as leakage during incubation in the plasma media. To further evaluate serum stability of ether-linked liposomes, following liposomal synthesis, samples are diluted into PBS or cell culture media (DMEM) containing 10% fetal bovine serum. The stability of the liposome can be determined by dynamic light scattering as well as by Scanning Electron Microscopy, for example at 0, 2, 4, 8, 12, 24, 48, 72 and 96 hours post-synthesis samples.

Long-term storage stability can be determined by diluting the stock solution (stored at 4° C.) periodically and measuring hydrodynamic size, using a Malvern Zetasizer Nano as described above. For this purpose, the stock can be diluted in saline (e.g., 154 mM NaCl) to give a final concentration of 1 mg/mL as described above. Samples are measured immediately after synthesis as well as post-synthesis intervals, for example, 3, 7, 14, 28, 60, 90, 180, 360 and 720, wherein the measurement generally consists of a 5 minute equilibration at 25° C. before a minimum of seven measurements are taken.

The pH stability of ether-linked liposomes in saline can be measured by batch-mode DLS using a Malvern Zetasizer Nano. Ether-linked formulations can be evaluated at pHs between 1-7 as compared to more traditional ester-linked formulations. To keep the ionic strength constant, 0.1 M HCl and 0.1 M NaOH should be prepared in saline (e.g., 154 mM NaCl). Samples of liposome formulations can be prepared by diluting the stock solution in saline (154 mM NaCl) to give a final concentration of 1 mg/mL. Solution pH can be adjusted and measured using an autotitrator before sample size is measured (for example, with a minimum of ten measurements). Similar experiments can be conducted to assess temperature stability.

In Vivo Studies:

Cellular insulin uptake and biological activity can be initially assessed in skeletal muscle cell cultures. Additional confirmatory cell culture studies can also utilize adipose cell lines. Uptake of ether-linked liposomal formulations verses "ghost" no-insulin liposomal controls, as well as free non-liposomal insulin can be investigated as a function of concentration (for example, in the range of about 1-100 ng/ml). Mass spectrometry as well as radioactive insulin can be utilized to assess cellular uptake of encapsulated and non-encapsulated insulin. Biological activity can be confirmed by conventional Western blotting of phosphorylated active forms of AKT and S6Kinase as well as the insulin receptor and IRS. Basic cellular toxicity can be assessed via survival, necrosis, and apoptotic assays.

To proceed to in vivo experiments, non-toxic insulin bioactivity can be demonstrated in cell cultures with the ether-linked liposomal formulations. If any signs of toxicology or lack of biological efficacy are observed, then further tests to improve cellular release of the API can be conducted. These strategies can include the addition of 10 molar percent cholesterol or cholesterol esters to the base formulation to increase "fusigenecity" of the formulations. Alternatively, a more targeted and less passive (PEGylated) approach can be considered as well as an approach that utilizes plasmalogenases to selectively hydrolyze ether-linked lipids.

In Vivo Experimentation:

The streptocytozin-treated Sprague Dawley rat model can be used to evaluate the in vivo toxicology and efficacy of orally administered insulin-encapsulated pH-resistant liposomes. This model is generally easier to gavage than mouse models, such as the Ins2akita mouse. It is somewhat problematic to ascertain the doses of orally gavaged insulin that must be administered to maintain glycemic control. Good control is normally achieved with the lin-plast (rat) implant (Lin Shin, Canada) or by intraperitoneal administration of 7 units total humulin three times a week to achieve less than 5½% HbA1c levels. Expressed another way, typically 0.25 U/ml will normalize blood glucose in diabetic rats when administered IP at 3 times body weight of animal. Thus, in an initial in vivo experiment, doses of free insulin and liposomally-encapsulated insulin (humulin) or control liposome at 6 doses ranging from 1 to 25 total units of insulin in cohorts consisting of groups of 5 rats can be administered by gavage to achieve statistical power. Encapsulated or free insulin or vehicle control can be administered three times a week over a week study and then assess total insulin content in the plasma by MS/MS, or by conventional ELISA. In a second set of experiments, an oral dose of encapsulated insulin equivalent to an IP dose that achieves good glycemic control can be evaluated in the diabetic model over a three month period. Insulin concentration in the blood stream can be quantified by mass spectrometry at the end of months 1, 2 and 3. Body weight and overt signs of toxicity can then be assessed. Blood glucose levels and HbA1c levels can be assessed by conventional methodologies at the end of months 1, 2 and 3. At the conclusion of the experiment, clinical pathology of pancreas, adipose, skeletal muscle, liver and cardiac and brain tissue as well as hematology and clinical chemistry can be initiated. Additional experiments beyond these proof-of-concept animal experiments can be used to evaluate MTD and other pharmacokinetic and biodistribution parameters in control Sprague Dawley rats.

Example 3: Development of an Acid Stable Liposomal Formulation of Insulin

Figure 11:
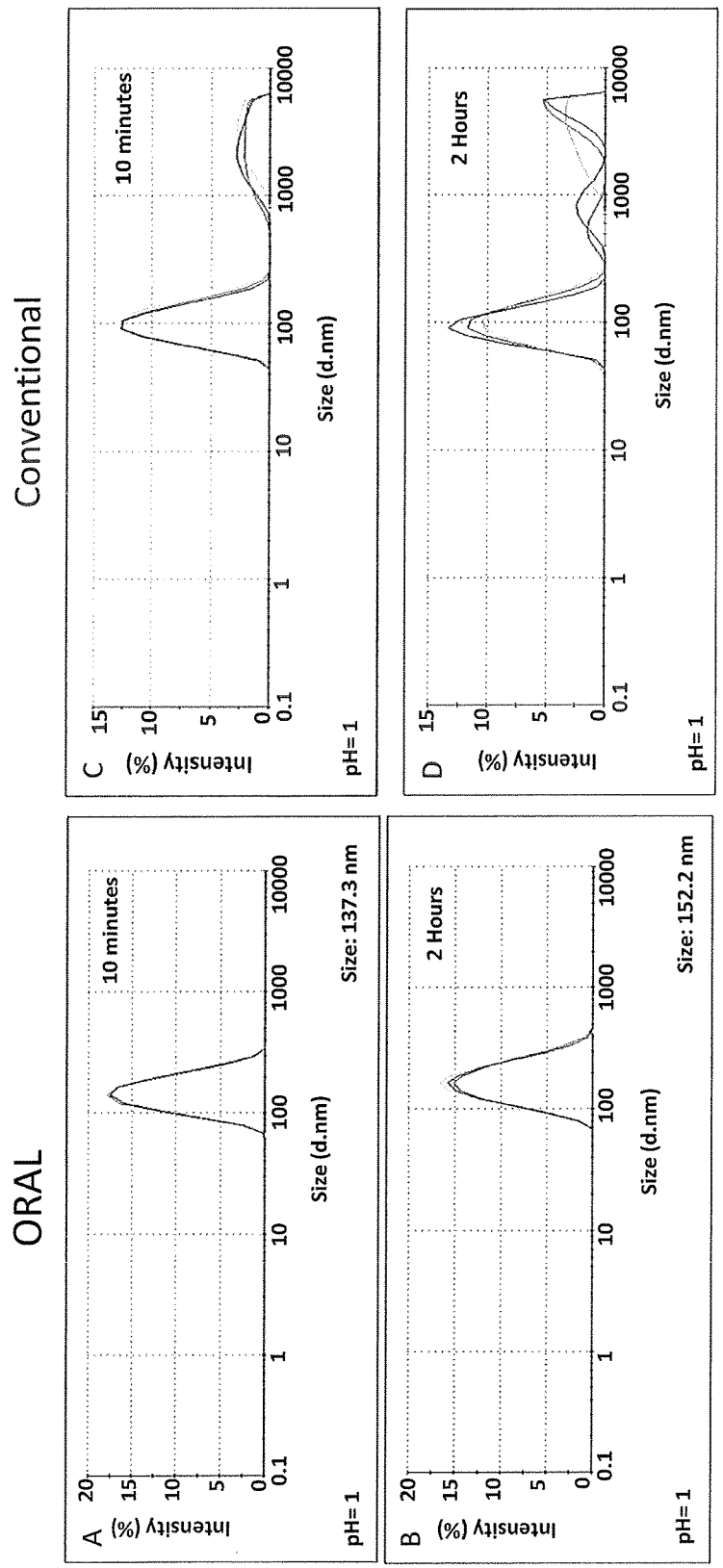
FIG. 11, comprising
Figures 12A, 12B, 12C:
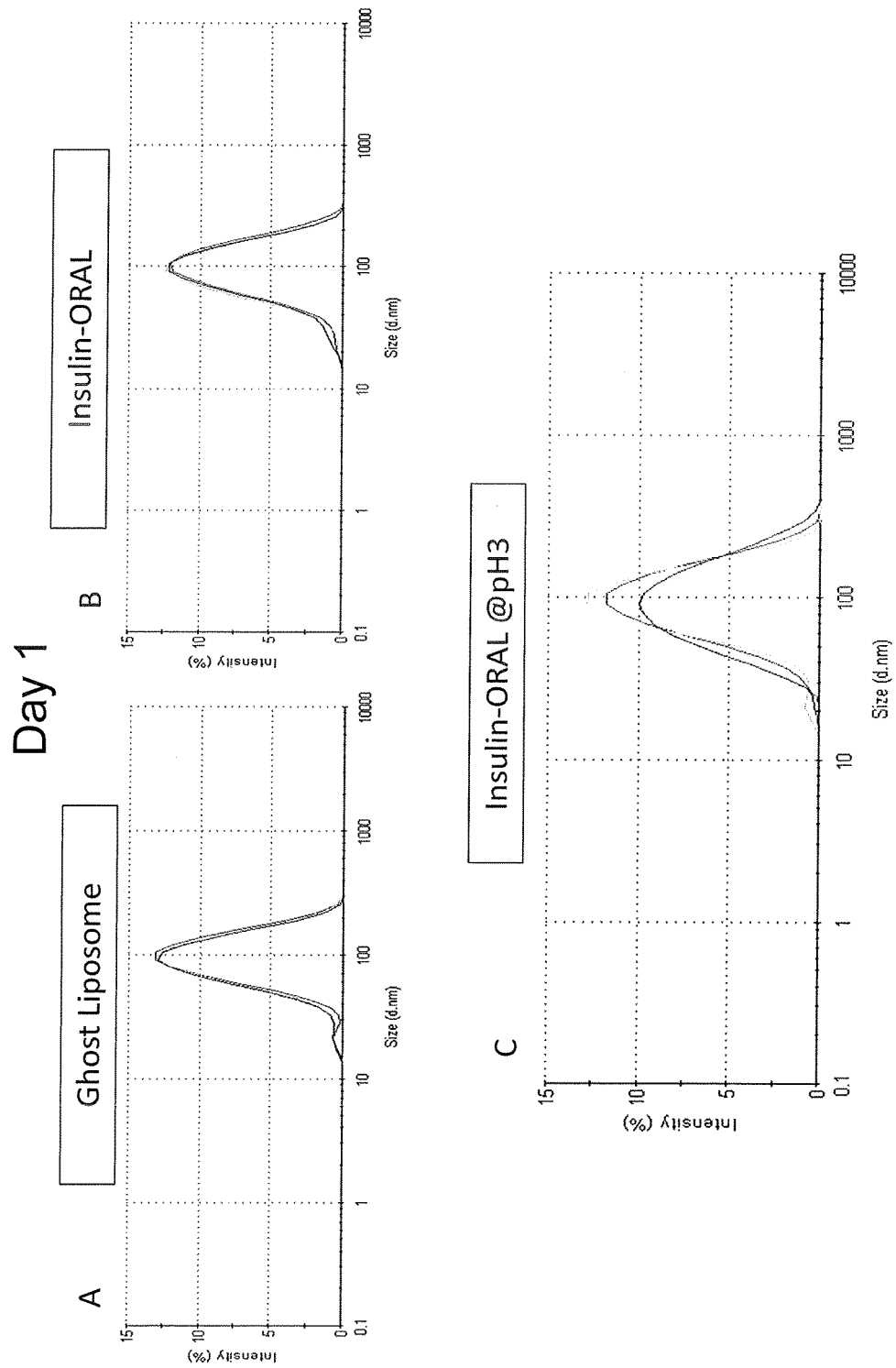
FIGS. 12A through 12D, is a set of graphs showing the sizing and stability of insulin-ORAL (FIGS. 12B through 12D) vs. a ghost liposome (FIG. 10A). Four batches of insulin-ORAL were produced which were monodispersed with a size of approximately 100 nm at pH 7 (FIG. 12B). When incubated for two hours (37° C.) at pH 3 insulin-ORAL maintained its size and integrity (FIG. 12C).
Figure 12D:
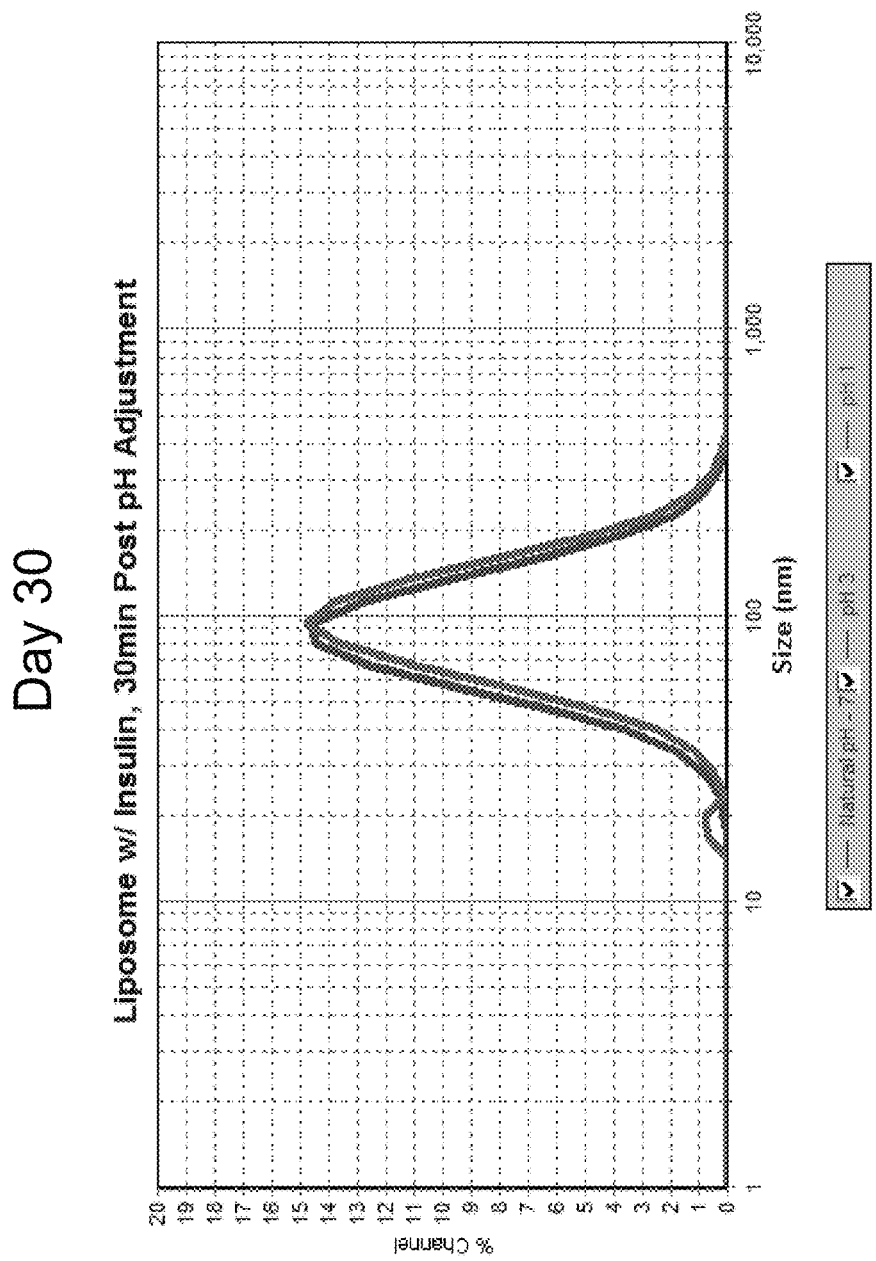

A liposomal formulation was prepared having a molar ratio of 5:3:2 1,2-di-O-hexadecyl-sn-glycero-3-phosphatidylcholine, 1,2-di-O-phytanyl-sn-glycero-3-phosphatidylethanolamine, and 1,2 distearoyl-phosphatidylethanolamine-PEG2000. These liposomes were made by drying the lipid solution under nitrogen for four hours, followed by rehydration in one milliliter of degassed PBS for 3 h at a temperature of 60° C. Then, natural physiological insulin was added at 1.2 mg/ml. The liposomes were sonicated for 20 sec at 60° C., until they became translucent. To ensure a homogenous distribution in size, the liposomal solution was manually extruded nine times through a 0.1 μm membrane with an Avanti Extruder at 60° C. Finally, the liposomes were columned through CL4B beads to remove any excess insulin that was not encapsulated, and the eluent was collected and centrifuged at 2000 RPM for 2 h and submitted to mass spectroscopy. Data related to the stability of this formulation are shown in FIGS. 11-12.

Figure 10:
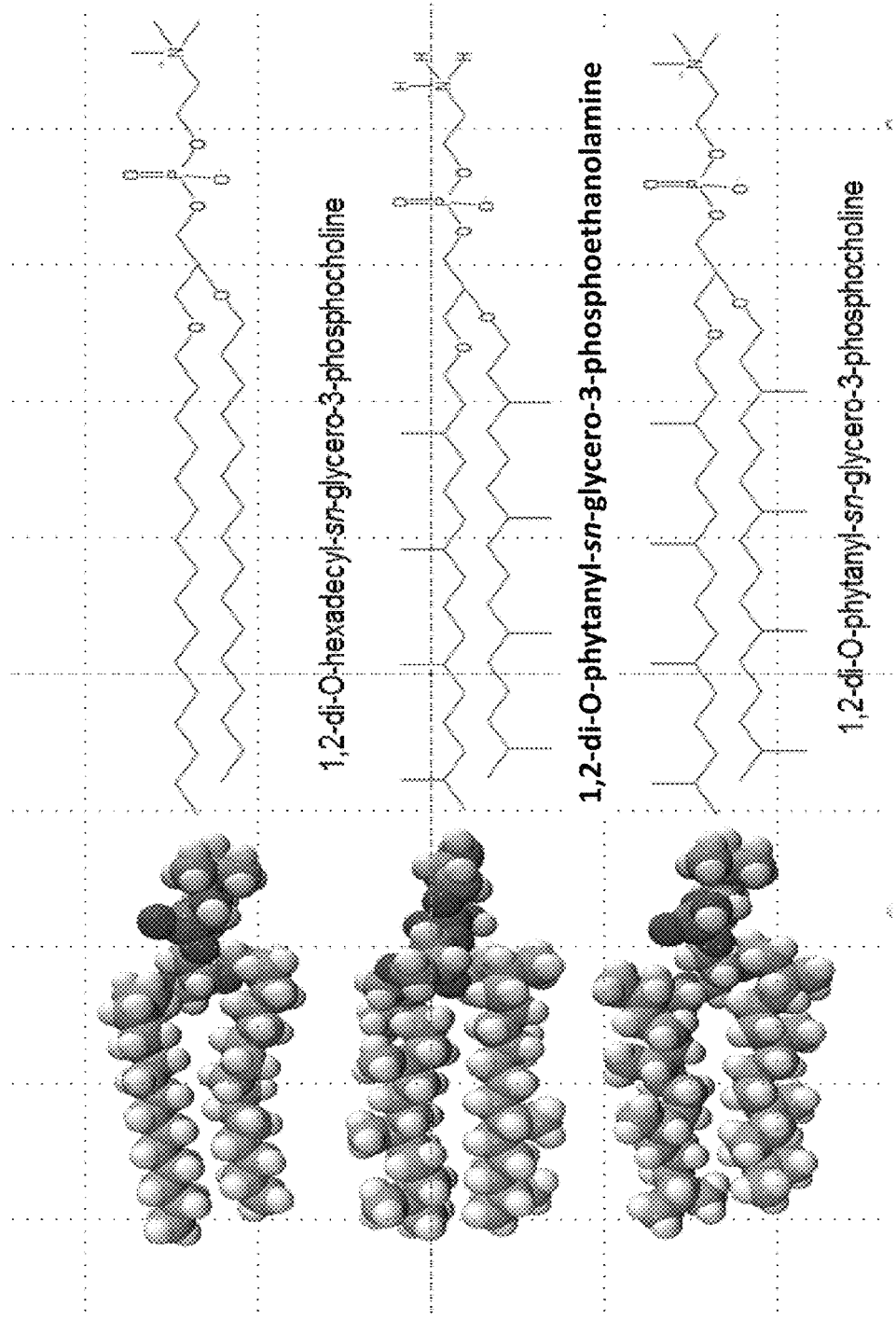
FIG. 10 is a schematic representation of the structure of exemplary ether lipids useful in the present invention.

In a preferred embodiment, the liposomal formulation can be prepared with PEGylated 1,2 di-O-phytanyl-sn-phosphatidylethanolamine instead of 1,2 distearoyl-phosphatidylethanolamine in the example above. The structures of non-PEGylated lipids useful for such a formulation are shown in FIG. 10.

In any of the embodiments described herein, the degree of PEGylation can be optimized to maximize the stability and insulin loading of the liposome formulation. In one embodiment, the degree of lipid PEGylation can be between 1 and 25 mol % PEG. Further, in various embodiments, the molecular weight of the PEG used can vary. In a preferred embodiment, the molecular weight of the PEG used for PEGylation of the lipids of the present invention can be in the range of about 2,000 to 10,000 Da.

Example 4: Biological Activity Assay for Insulin-ORAL

To determine biological activity and cellular uptake of insulin-oral liposomes a western blotting assay was performed for phosphorylated active forms of S6Kinase.

Figure 13:
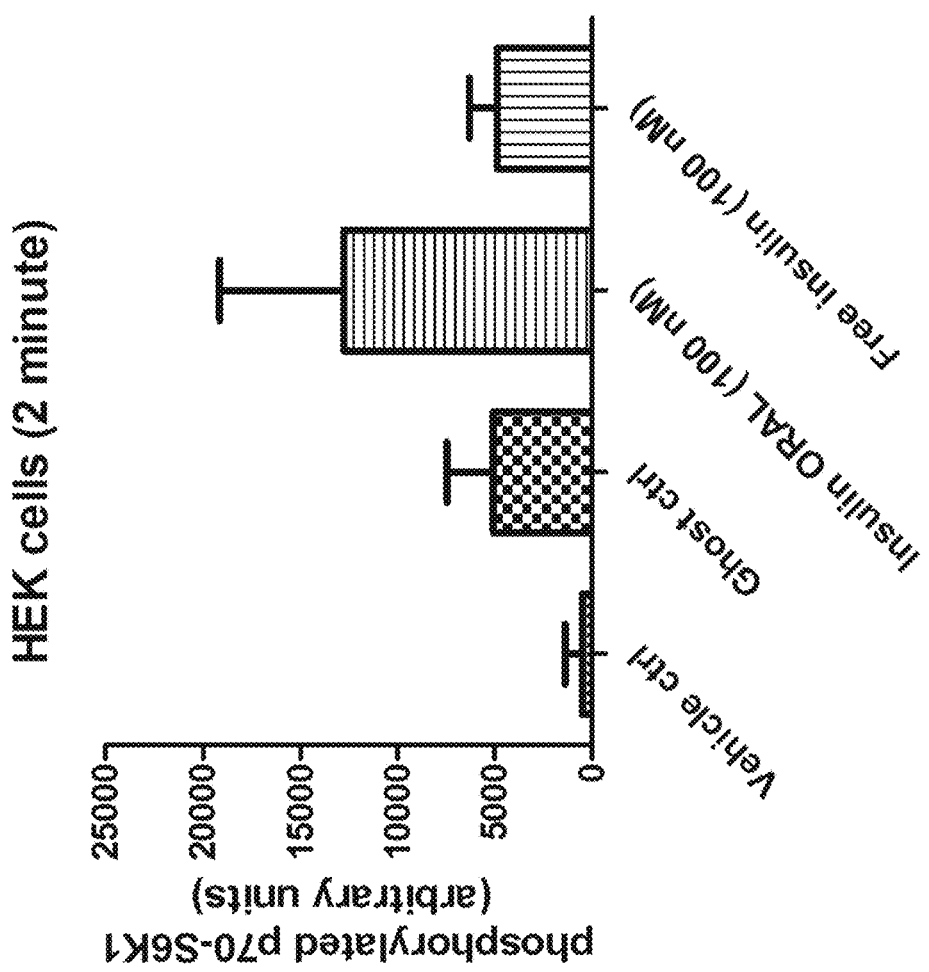
FIG. 13 is a graph showing biological activity assay data in HEK cells for insulin-ORAL and free insulin.

Human embryonic kidney 293 cells (HEK 293 cells) cell cultures were grown up under conventional conditions. The cell cultures were serum starved for 24 hours prior to addition of the compositions described below. Four different compounds were added to the cell cultures for 2 minutes: a) a vehicle control (no lipids); b) a ghost liposome control having an equivalent amount of identical lipids at the same concentration without insulin present; c) insulin-ORAL with insulin present in the liposome at 100 ng/mL and d) free insulin also at 100 ng/mL. The results show that insulin-ORAL is more bioactive than free insulin at equimolar doses or the ghost control N=3±SD of the mean. Results are presented in FIG. 13.

Figure 14:
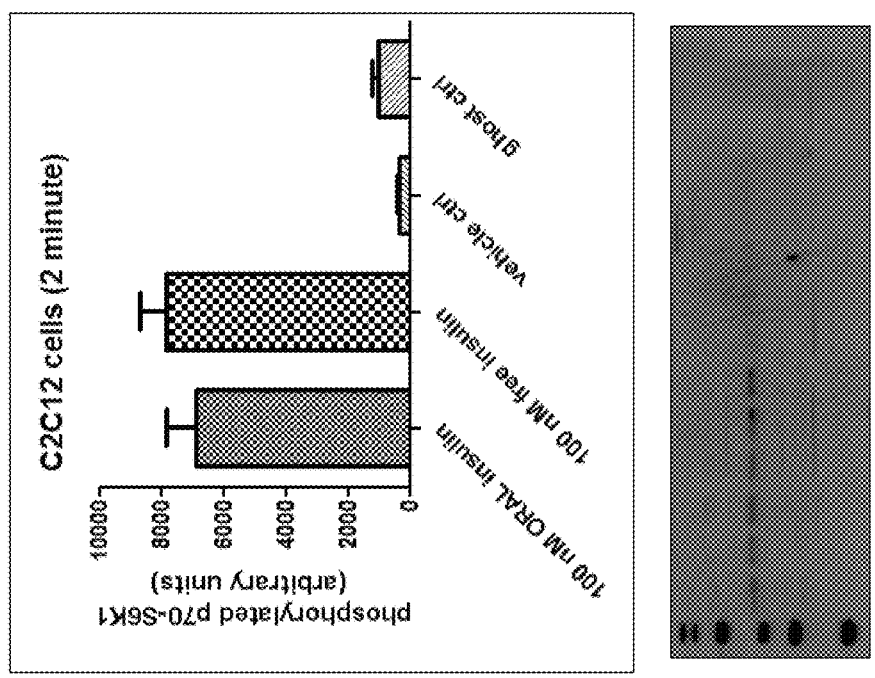
FIG. 14 is a graph (FIG. 14A) and probe assay (FIG. 14B) showing insulin-ORAL myoblast cell data.

Insulin-ORAL or free insulin (as well as appropriate controls) were added to C2C12 myoblast cell cultures for 2 min at 37° C. and then lysates were probed for phosphorylated p70-S6kinase activity, a surrogate for insulin receptor activation, n=3 replicates. As shown in FIG. 14, insulin-ORAL was as effective as free insulin at equimolar dosing.

Stability Testing by Dynamic Light Scattering for PEGylated Ghost and Insulin-Oral Liposomes.

Figure 15:
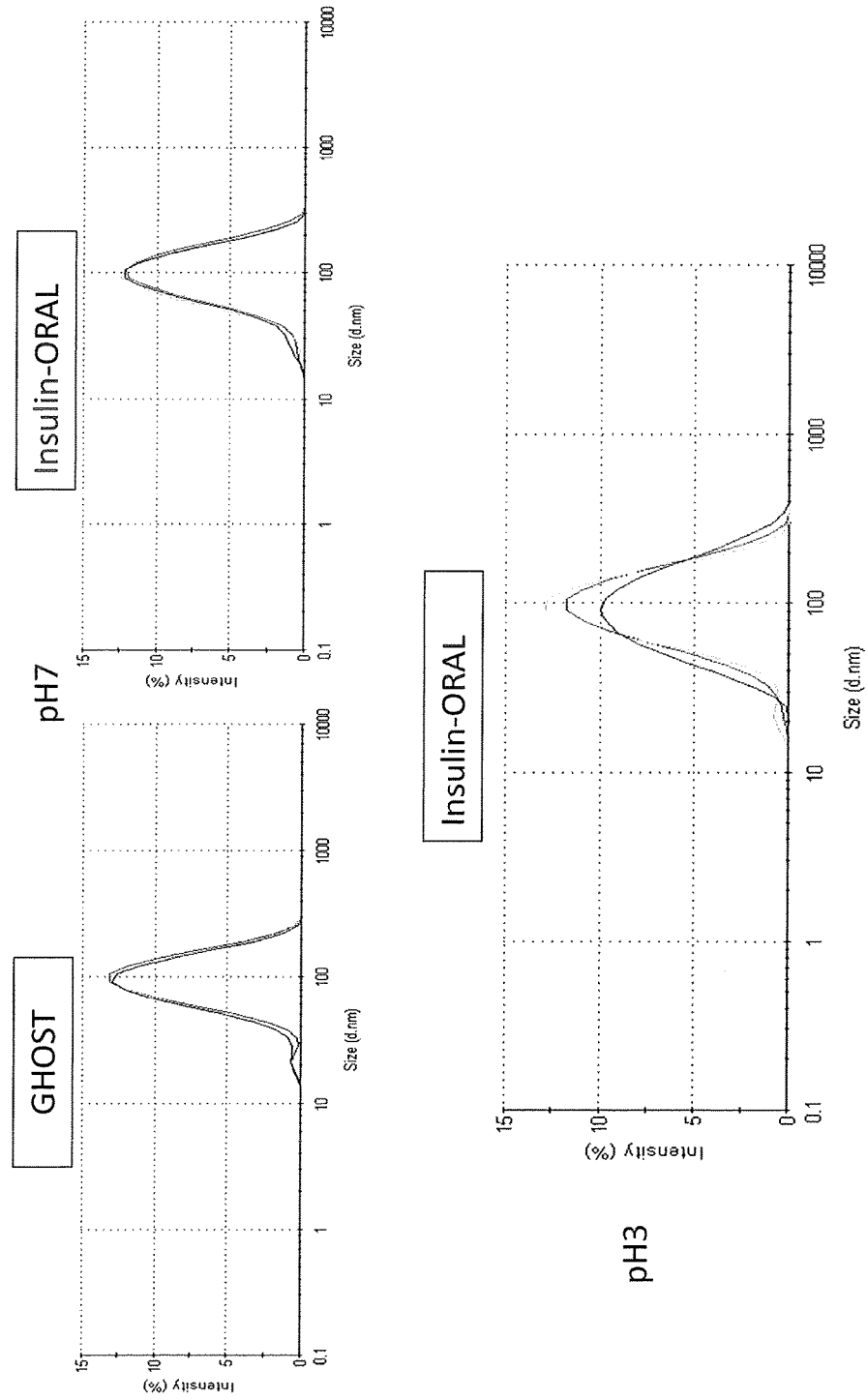
FIGS. 15, 16, and 17 are a series of graphs showing stability testing results for PEGylated ghost and insulin-ORAL liposomes. Tests were run at different pHs and at different time points: 1 day (FIG. 15), 63 days (FIG. 16), and 97 days (FIG. 17).
Figure 16:
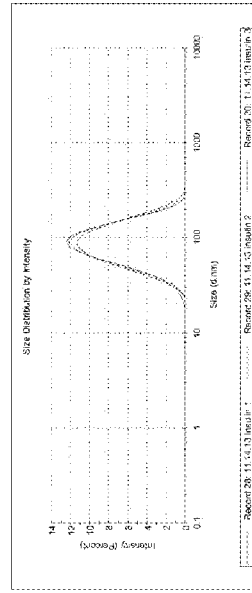
Figure 16:
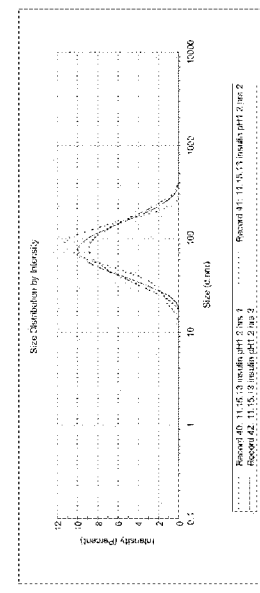
Figure 16:
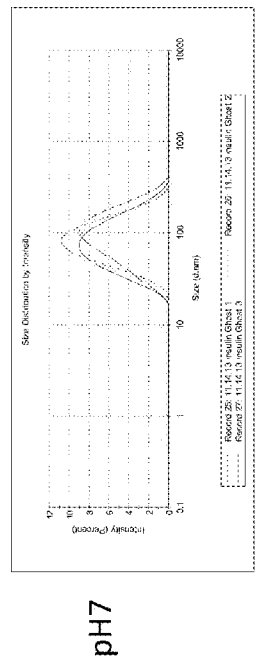
Figure 16:
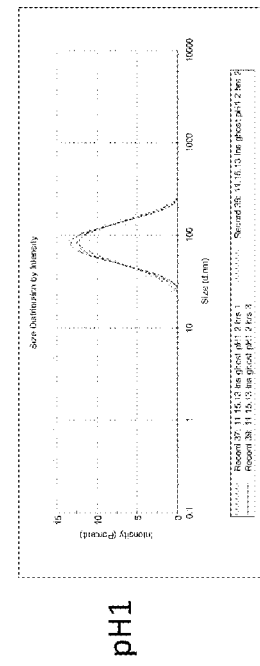
Figure 17:
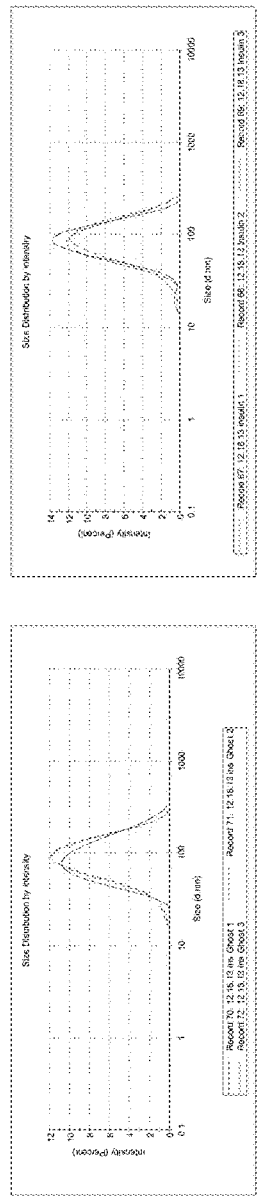
Figure 17:
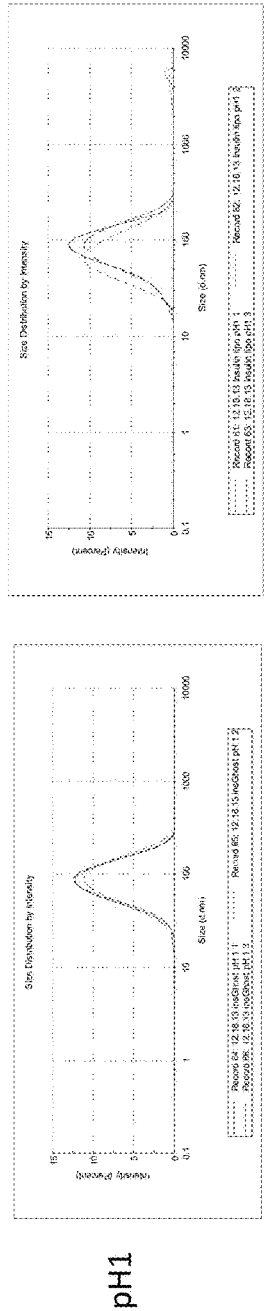

Tests were run at three time points (days 1, 63, and 97, see FIGS. 15 through 17) and at several pHs for 2 hrs. Formulations were 1,2-di-O-hexadecyl-sn-glycero-3-phosphatidylcholine/1,2-di-O-phytanyl-sn-glycero-3-phosphatidylethanolamine/1,2-di-O-phytanyl-sn-glycero-3-phosphatidylethanolamine-PEG2000 (DHPC/DPPE/PEG2000-DSPE) 4.5/4/1.5 V/V/V. which encapsulated 60% 1 mg/ml exogenous insulin. It was demonstrated that nanoscale PEGylated ORAL liposomes can be formed and are stable for PEGylation ratios ranging from 0-20%, However maximal loading efficiencies (>60) were noted with the preferred embodiment, i.e., 15 molar percent. Likewise, nanoscale PEGylated ORAL liposomes can be formed and are stable for total PC/PE ratios of 2/1 to 2/3, with a preferred embodiment of 9/11 showing maximal loading efficiency for insulin. Formulations designed to improve loading efficiency included 5 molar percent of the anionic phospholipid DHPA. These formulations also formed liposomes and were stable.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A liposomal formulation comprising 1,2-di-O-hexadecyl-sn-glycero-3-phosphatidylcholine and 1,2-di-O-phytanyl-sn-glycero-3-phosphatidylethanolamine, wherein the 1,2-di-O-hexadecyl-sn-glycero-3-phosphatidylcholine and 1,2-di-O-phytanyl-sn-glycero-3-phosphatidylethanolamine form uniformly sized particles; wherein the molar ratio of 1,2-di-O-hexadecyl-sn-glycero-3-phosphatidylcholine: 1,2-di-O-phytanyl-sn-glycero-3-phosphatidylethanolamine of the formulation is in the range of 2:1 to 2:3; and wherein the liposomal formulation is stable at a pH of at least 1.

2. The liposomal formulation of claim 1, wherein the particles comprise: liposomes, nanoliposomes, niosomes, microspheres, nanospheres, nanoparticles, micelles or archaeosomes.

3. The liposomal formulation of claim 2, wherein the uniformly-sized particles encapsulate a bioactive agent.

4. The liposomal formulation of claim 3, wherein the bioactive agent is insulin or a pro-drug thereof.

5. The liposomal formulation of claim 3, having a molar ratio of: 1,2-di-O-hexadecyl-sn-glycero-3-phosphatidylcholine, 1,2-di-O-phytanyl-sn-glycero-3-phosphatidylethanolamine and bioactive agent of 6:3:1.

6. The liposomal formulation of claim 3, wherein the bioactive agent is docosahexanoic acid (DHA).

7. The liposomal formulation of claim 3, wherein the uniformly-sized particles further comprise a PEGylated lipid.

8. The liposomal formulation of claim 7, wherein the uniformly-sized particles comprise up to 20 molar percent of the PEGylated lipid.

9. The liposomal formulation of claim 7, wherein the PEGylated lipid is 1,2-di-O-phytanyl-sn-glycero-3-phosphatidylethanolamine-PEG2000.

10. The liposomal formulation of claim 7, wherein the PEGylated lipid is 1,2 distearoyl-phosphatidylethanolamine-PEG2000.

11. The liposomal formulation of claim 7, wherein the formulation has a molar ratio of 1,2-di-O-hexadecyl-sn-glycero-3-phosphatidylcholine: 1,2-di-O-phytanyl-sn-glycero-3-phosphatidylethanolamine: PEGylated lipid of 5:3:2.

12. The liposomal formulation of claim 7, wherein the formulation has a molar ratio of: 1,2-di-O-hexadecyl-sn-glycero-3-phosphatidylcholine: 1,2-di-O-phytanyl-sn-glycero-3-phosphatidylethanolamine: PEGylated lipid of 4.5:4.0:1.5.

* * * * *